US012747318B2

(12) United States Patent
Moore et al.

(10) Patent No.: US 12,747,318 B2
(45) Date of Patent: Sep. 29, 2026

(54) EFFICIENT METHOD OF SYNTHESIZING LINEAR OLIGOMERS AND APPLICATION TO FRONTAL RING-OPENING METATHESIS POLYMERIZATION

(71) Applicant: The Board of Trustees of the University of Illinois, Urbana, IL (US)

(72) Inventors: Jeffrey S. Moore, Urbana, IL (US); Nancy R. Sottos, Urbana, IL (US); Benjamin A. Suslick, Urbana, IL (US); Diego M. Alzate-Sanchez, Urbana, IL (US); Nil A. Parikh, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 690 days.

(21) Appl. No.: 18/310,155

(22) Filed: May 1, 2023

(65) Prior Publication Data

US 2023/0357490 A1 Nov. 9, 2023

Related U.S. Application Data

(60) Provisional application No. 63/337,450, filed on May 2, 2022.

(51) Int. Cl.

*C08G 61/08* (2006.01)
*C07C 2/04* (2006.01)

(Continued)

(52) U.S. Cl.

CPC ................ *C08G 61/08* (2013.01); *C07C 2/04* (2013.01); *C07C 29/44* (2013.01); *C07C 67/08* (2013.01)

(58) Field of Classification Search

CPC ......... C08G 61/00; C08G 61/06; C08G 61/08

See application file for complete search history.

(56) References Cited

U.S. PATENT DOCUMENTS 4,933,402 A * 6/1990 Matlack ................. C08G 61/08 264/328.2

5,741,869 A * 4/1998 Goodall .................. C08F 32/08 526/171

(Continued)

FOREIGN PATENT DOCUMENTS

EP 2 982 709 A1 2/2016

EP 3 199 577 A1 8/2017

(Continued)

OTHER PUBLICATIONS

WO-2020099750-A1 (May 22, 2020); machine translation. (Year: 2020).*

(Continued)

*Primary Examiner* — Rip A Lee

(74) *Attorney, Agent, or Firm* — Crowell & Moring LLP

(57) ABSTRACT

Methods of preparing oligomers including heating a mixture of an amount of a functionalized cycloalkene, an amount of a chain transfer agent, a phosphite ester, and a catalyst, a degree of polymerization of the oligomers controllable by a molar ratio of the amount of the functionalized cycloalkene to the amount of the chain transfer agent, are provided herein. Methods of preparing polymers including heating the oligomers and a second amount of the functionalized (Continued)

cycloalkene, a phosphite ester, and a catalyst are further provided. Compositions of oligomers and functionalized cycloalkenes are further provided.

23 Claims, 23 Drawing Sheets

(51) Int. Cl.

| | |
|---|---|
| ***C07C 29/44*** | (2006.01) |
| ***C07C 67/08*** | (2006.01) |
| ***C08G 61/00*** | (2006.01) |

(56) References Cited

U.S. PATENT DOCUMENTS

| | | | | |
|---|---|---|---|---|
| 5,939,504 | A * | 8/1999 | Woodson, Jr. | C08G 61/08 556/136 |
| 9,309,344 | B2 * | 4/2016 | Kadyrov | C08F 4/80 |
| 10,017,615 | B2 * | 7/2018 | Drozdzak Matusiak | C08K 7/14 |
| 11,926,696 | B2 * | 3/2024 | Metzger | C08G 59/00 |
| 2021/0246260 | A1 * | 8/2021 | Metzger | C09J 4/00 |
| 2021/0253784 | A1 | 8/2021 | Metzger et al. | |

FOREIGN PATENT DOCUMENTS

| | | | | |
|---|---|---|---|---|
| EP | 3202813 | A1 * | 8/2017 | C08G 61/08 |
| JP | H07258390 | A1 | 10/1995 | |
| WO | WO-2020099750 | A1 * | 5/2020 | C08G 61/08 |
| WO | WO 2022/212752 | A1 | 10/2022 | |

OTHER PUBLICATIONS

International Preliminary Report on Patentability and Written Opinion of the International Searching Authority in International Application No. PCT/US2023/066430, dated Oct. 29, 2024 (11 pages).

Notification of Transmittal of the International Search Report and The Written Opinion of the International Searching Authority and the International Search Report and Written Opinion dated Aug. 9, 2023, received in PCT Application No. PCT/US2023/066430 (22 pages).

Dean, L., et al. "Rapid Synthesis of Elastomers and Thermosets with Tunable Thermomechanical Properties" *ACS Macro Letters*, 2020, 9, pp. 819-824 (6 pages).

Robertson, I., et al. "Frontal Ring-Opening Metathesis Polymerization of Exo-Dicyclopentadiene for Low Catalyst Loadings" *ACS Macro Letters*, 2016, 5, pp. 593-596 (4 pages).

Liu, H., et al. "Frontal Ring-Opening Metathesis Copolymerization: Deviation of Front Velocity from Mixing Rules" *ACS Macro Letters*, 2019, 8, pp. 846-851 (7 pages).

Robertson, I., et al. "Alkyl Phosphite Inhibitors for Frontal Ring-Opening Metathesis Polymerization Greatly Increase Pot Life" *ACS Macro Letters*, 2017, 6, pp. 609-612 (4 pages).

Robertson, I., et al. "Rapid Energy-Efficient Manufacturing of Polymers and Composites Via Frontal Polymerization" *Nature*, vol. 557, May 10, 2018 (13 pages).

* cited by examiner i = ii = iii =

R'' = H, H, $C_2H_4OH$, $C_2H_4OH$, $C_2H_4OH$, $C_2H_4OH$, $C_2H_4OH$ i = ii =

Nor =

EFFICIENT METHOD OF SYNTHESIZING LINEAR OLIGOMERS AND APPLICATION TO FRONTAL RING-OPENING METATHESIS POLYMERIZATION

CROSS-REFERENCE TO RELATED APPLICATIONS

The present application claims the benefit of U.S. Provisional Application No. 63/337,450, filed May 2, 2022, the entirety of which is incorporated by reference herein for all purposes.

STATEMENT REGARDED FEDERALLY FUNDED RESEARCH

This invention was made with government support under award 1933932 awarded by the National Science Foundation, FA9550-16-1-0017 awarded by the U.S. Air Force, DE-SC0023457 and DE-AR0001330 subaward 102726 awarded by the Department of Energy. The government has certain rights in the invention.

TECHNICAL FIELD

The present disclosure relates to processes of preparing oligomers and polymers from compositions.

BACKGROUND

Oligomers and polymers of dicyclopentadiene ("DCPD") are conventionally generated via ring-opening metathesis polymerization ("ROMP"), with curing occurring concurrently with linear polymer formation. ROMP methods typically rely on dilute conditions with high catalyst loadings, are not scalable, and produce a distribution of species with varying end-groups that limit subsequent applications of the product. Some other ROMP methods may result in low total conversion.

Current three-dimensional printing strategies involve fumed silica as a thickener, which may introduce challenges associated with maintaining a constant viscosity. Further, fumed silica may negatively interact with a catalyst formulation, thereby altering the reactivity profile of a catalyst.

There is a need for the development of methods that provide soluble and processable oligomers of DCPD, that are scalable, and that demonstrate high conversion. Further, there is a need for the development of concentrated or solvent-less reaction conditions to provide oligomers of DCPD. Further, there is a need for rheological modifiers for three-dimensional printing applications that do not affect the reactivity profile of a catalyst.

SUMMARY

In an example, the present disclosure provides a method for preparing oligomers. The method includes: adding an amount of a phosphite ester and an amount of a catalyst to an amount of a functionalized cycloalkene and an amount of a chain transfer agent to provide a mixture; and heating the mixture to produce the oligomers. The chain transfer agent is a monosubstituted olefin.

A degree of polymerization of the oligomers is controllable by a molar ratio of the amount of the functionalized cycloalkene to the amount of the chain transfer agent.

In another example, the present disclosure provides a method for preparing oligomers of formula (I):

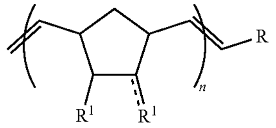

(I)

The method includes: adding an amount of a phosphite ester of formula $P(OR^3)_3$ and an amount of a catalyst to an amount of dicyclopentadiene and an amount of a chain transfer agent to provide a mixture; and heating the mixtures to produce the oligomers of formula (I). R is a straight-chain, branched, or cyclic ($C_1$-$C_{20}$)alkyl group, or an aryl, heteroaryl, or heterocyclic group. Each $R^1$ is independently hydrogen, a straight-chain, branched, or cyclic ($C_1$-$C_{20}$) alkyl or ($C_{1-20}$)alkenyl group, or the two $R^1$ groups together may form a cycloalkyl or cycloalkenyl structure, together with the carbons to which the $R^1$ groups are attached. The ⎓ bond represents an optional double bond, provided that when a double bond is present, the $R^1$ at one end of the double bond is not hydrogen. $R^3$ are all simultaneously or each independently methyl, ethyl, n-butyl, tert-butyl, or phenyl. The chain transfer agent is a monosubstituted olefin of formula (II):

(II)

wherein $R^2$ is a straight-chain, branched, or cyclic ($C_1$-$C_{20}$) alkyl group or ($C_1$-$C_{20}$)alkoxy group, or an aryl, heteroaryl, or heterocyclic group, optionally substituted with a halogen atom, a hydroxy group, a boronate ester group, an epoxy group, an acrylate group, an ester group, or an amide group.

A degree of polymerization of the oligomers of formula (I) is controllable by a molar ratio of the amount of dicyclopentadiene to the amount of the chain transfer agent.

In yet another example, the present disclosure provides a composition. The composition includes dicyclopentadiene and oligomers of formula (I):

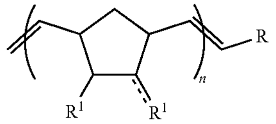

(I)

The oligomers of formula (I) are in an amount of from about 20 weight % to about 80 weight % based on a combined weight % of the oligomers of formula (I) and the dicyclopentadiene. R is a straight-chain, branched, or cyclic ($C_1$-$C_{20}$)alkyl group, or an aryl, heteroaryl, or heterocyclic group. Each $R^1$ is independently hydrogen, a straight-chain, branched, or cyclic ($C_1$-$C_{20}$)alkyl or ($C_{1-20}$)alkenyl group, or the two $R^1$ groups together may form a cycloalkyl or cycloalkenyl structure, together with the carbons to which the $R^1$ groups are attached. The ⎓ bond represents an optional double bond, provided that when a double bond is present, the $R^1$ at one end of the double bond is not hydrogen. One or both of the $R^1$ groups of one monomer may be different than one or both of the $R^1$ groups of an adjacent monomer. A number-average degree of polymerization of the oligomers of formula (I) is from 3 to 30.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

In order that the present disclosure may be well understood, there will now be described various forms thereof, given by way of example, reference being made to the accompanying drawings. The components in the figures are not necessarily to scale.

Figure 1A:
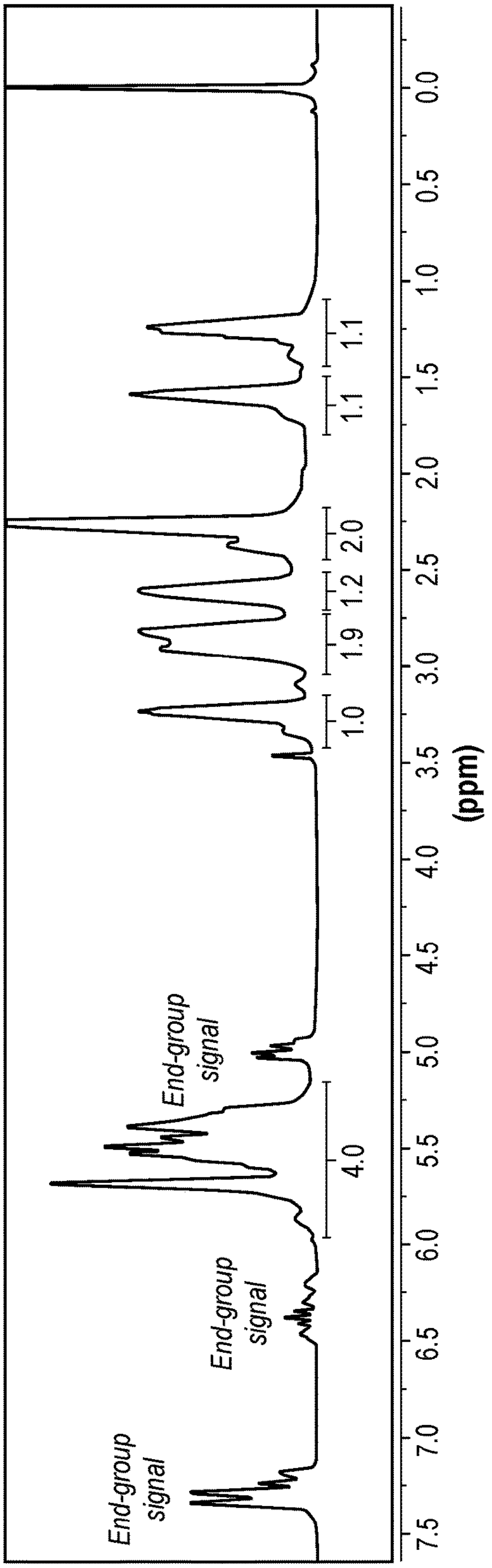
FIG. 1A illustrates a $^{1}$H NMR spectrum (499.7 MHz, chloroform-d with 1% v/v $SiMe_4$) of o(DCPD) derived from Formulation 1.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

The uses of the terms "a" and "an" and "the" and similar referents in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by Applicant to the contrary, to mean a quantity of more than one. All methods described herein may be performed in any suitable order unless otherwise indicated herein by context.

As will be understood by one skilled in the art, for any and all purposes, all ranges recited herein also encompass any and all possible sub-ranges and combinations of sub-ranges thereof, as well as the individual values making up the range, particularly integer values. It is therefore understood that each unit between two particular units is also disclosed. For example, if "10 to 15" is disclosed, then 11, 12, 13, and 14 are also disclosed, individually, and as part of a range. A recited range (for example, weight percentages or carbon groups) includes each specific value, integer, decimal, or identity within the range. Any listed range may be easily recognized as sufficiently describing and enabling the same range being broken down into at least equal halves, thirds, quarters, fifths, or tenths. As will also be understood by one skilled in the art, all language such as "up to," "at least," "greater than," "less than," "more than," "or more," and the like, include the number recited and such terms refer to ranges that may be subsequently broken down into sub-ranges. In the same manner, all ratios recited herein also include all sub-ratios falling within the broader ratio. Accordingly, specific values recited for radicals, substituents, and ranges are for illustration only; the specific values do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or examples whereby any one or more of the recited elements, species, or examples may be excluded from such categories or examples, for example, for use in an explicit negative limitation.

As used herein, the terms "comprise(s)," "include(s)," "having," "has," may, "contain(s)," and variants thereof, are intended to be open-ended transitional phrases, terms, or words that do not preclude the possibility of additional acts or structures. The present description also contemplates other examples "comprising," "consisting of," and "consisting essentially of," the examples or elements presented herein, whether explicitly set forth or not.

In describing elements of the present disclosure, the terms "$1^{st}$," "$2^{nd}$," "first," "second," "A," "B," "(a)," "(b)," and the like may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or +5%, among others, would satisfy the definition of "about," unless more narrowly defined in particular instances.

The term "alkyl," by itself or as part of another substituent, refers, unless otherwise stated, to a straight, branched, or cyclic chain aliphatic hydrocarbon ("cycloalkyl") monovalent radical having the number of carbon atoms designated (in other words, "$C_1$-$C_{20}$" means one to twenty carbons, and includes $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, and $C_{19}$). Examples include methyl, ethyl, propyl, isopropyl, cyclopropyl, butyl, isobutyl, sec-butyl, tert-butyl, cyclobutyl, methylcyclopropyl, cyclopropylmethyl, pentyl, neopentyl, hexyl, and cyclohexyl.

The term "alkoxy," by itself or as part of another substituent, refers, unless otherwise stated, an alkyl group having the designated number of carbon atoms, as defined above, connected to the rest of a molecule via an oxygen atom, such as, for example, methoxy, ethoxy, 1-propoxy, 2-propoxy ("isopropoxy"), and the higher homologs and isomers.

Each of the terms "alkene" and "olefin," by itself or as part of another substituent, refers, unless otherwise stated, to a stable mono-unsaturated or di-unsaturated or poly-unsaturated straight chain, branched chain, or cyclic hydrocarbon ("cycloalkene"), "unsaturated" meaning a carbon-carbon double bond (—CH═CH—). "Monosubstituted" alkenes include only one bond between an alkene double-bonded carbon and an adjacent carbon, such as, for example, $CH_2$═CH—C. "Disubstituted" alkenes include two bonds between an alkene double-bonded carbon and adjacent carbons, and the adjacent carbons may be bonded to one ($CH_2$═$CC_2$) or both (C—CH═CH—C) of the alkene double-bonded carbons. "Trisubstituted" alkenes include three bonds between alkene double-bonded carbons and adjacent carbons (CH═$CC_2$). "Tetrasubstituted" alkenes include four bonds between alkene double-bonded carbons and adjacent carbons ($CC_2$═$CC_2$).

The term "alkenyl," by itself or as part of another substituent, refers to a stable mono-unsaturated or di-unsaturated or poly-unsaturated straight chain, branched chain, or cyclic hydrocarbon monovalent radical having the number of carbon atoms designated. Examples may include vinyl, propenyl, allyl, crotyl, isopentenyl, butadienyl, 1,3-pentadienyl, 1,4-pentadienyl, cyclopentenyl, cyclopentadienyl, and the higher homologs and isomers.

The term "functionalized," in the context of cycloalkenes, refers, unless otherwise stated, to a cycloalkene being ring-strained or having a nonhydrocarbon substituent on one or more of the carbons of the cyclic moiety of the cycloalkene.

The term "ring-strained," in the context of cycloalkenes, refers, unless otherwise stated, to the relative higher energy of a cycloalkene as a result of the number of carbons making up one or more of the cyclic moieties of the cycloalkene causing compression or "strain" to the natural angles between carbon-carbon bonds at each carbon atom of the one or more cyclic moieties, wherein the compression or strain would be alleviated (and the energy would be decreased) were the one or more cyclic moieties to undergo a reaction that would "open" the ring at the alkene bond.

The term "aromatic" generally refers to a carbocycle or heterocycle having one or more polyunsaturated rings having aromatic character (in other words, having (4n+2) delocalized π (pi) electrons where n is an integer).

The term "aryl," by itself or in combination with another substituent, refers, unless otherwise stated, to a carbocyclic aromatic system substituent containing one or more rings (typically one, two, or three rings), wherein such rings may be attached together in a pendant manner, such as biphenyl, or may be fused, such as naphthalene. Examples may include phenyl, benzyl, anthracyl, and naphthyl. Preferred are phenyl, benzyl, and naphthyl; most preferred are phenyl and benzyl.

The terms "heterocyclic," "heterocycle," and "heterocyclyl," by themselves or in combination with another substituent, refer, unless otherwise stated, to a stable, mono- or multi-cyclic ring system that consists of carbon atoms and at least one heteroatom independently selected from N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. Non-limiting examples of monocyclic heterocyclic groups include: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxidine.

The terms "heteroaryl" and "heteroaromatic," by themselves or in combination with another substituent, refer, unless otherwise stated, to a heterocyclic having aromatic character. Non-limiting examples of monocyclic heteroaryl groups include: pyridyl; pyrazinyl; pyrimidinyl, particularly 2- and 4-pyrimidinyl; pyridazinyl; thienyl; furyl; pyrrolyl, particularly 2-pyrrolyl; imidazolyl; thiazolyl; oxazolyl; pyrazolyl, particularly 3- and 5-pyrazolyl; isothiazolyl; 1,2,3-triazolyl; 1,2,4-triazolyl; 1,3,4-triazolyl; tetrazolyl; 1,2,3-thiadiazolyl; 1,2,3-oxadiazolyl; 1,3,4-thiadiazolyl; and 1,3,4-oxadiazolyl.

Polycyclic heterocycles include both aromatic and non-aromatic polycyclic heterocycles, non-limiting examples of which include: indolyl, particularly 3-, 4-, 5-, 6-, and 7-indolyl; indolinyl; indazolyl, particularly 1H-indazol-5-yl; quinolyl; tetrahydroquinolyl; isoquinolyl, particularly 1- and 5-isoquinolyl; 1,2,3,4-tetrahydroisoquinolyl; cinnolyl; quinoxalinyl, particularly 2- and 5-quinoxalinyl; quinazolinyl; phthalazinyl; naphthyridinyl, particularly 1,5- and 1,8-naphthyridinyl; 1,4-benzodioxanyl; coumaryl; dihydrocoumaryl; benzofuryl, particularly 3-, 4-, 5-, 6-, and 7-benzofuryl; 2,3-dihydrobenzofuryl; 1,2-benzoisoxazoyl; benzothienyl, particularly 3-, 4-, 5-, 6-, and 7-benzothienyl; benzoxazolyl; benzothiazolyl, particularly 2- and 5-benzothiazolyl; purinyl; benzimidazolyl, particularly 2-benzimidazolyl; benztriazolyl; thioxanthinyl; carbazolyl; carbolinyl; acridinyl; pyrrolizidinyl; pyrrolo[2,3-b]pyridinyl, particularly 1H-pyrrolo[2,3-b]pyridin-5-yl; and quinolizidinyl. Particularly preferred are 4-indolyl, 5-indolyl, 6-indolyl, 1H-indazol-5-yl, and 1H-pyrrolo[2,3-b]pyridin-5-yl.

The term "halogen," by itself or as part of another substituent, refers, unless otherwise stated, to a monovalent fluorine, chlorine, bromine, or iodine atom.

The term "boronate ester group" refers to a functional group, moiety, or substituent that is substituted for a hydrogen atom of an organic compound, and is of formula (III):

(III)

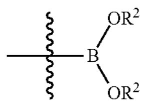

wherein each $R^2$ is independently a straight-chain, branched, or cyclic ($C_1$-$C_{20}$)alkyl group, or an aryl, heteroaryl, or heterocyclic group, or together with boron and oxygen, the $R^2$ groups form a cyclic moiety; and

is the point of attachment of the boronate ester group to a carbon of the organic compound. Examples of boronate ester groups may include boronic acid pinacol ester and boronic acid trimethylene glycol ester:

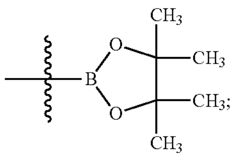

boronic acid pinacol ester

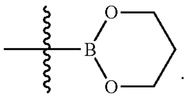

boronic acid trimethylene glycol ester

The term "epoxy group" refers to a non-aromatic, heterocyclic functional group, moiety, or substituent of an organic compound in which the heterocycle is characterized by three atoms connected by single bonds, two of the atoms being carbon and the third being oxygen. The general structural formula of an epoxy group is:

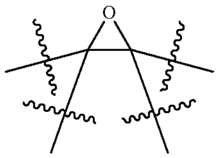 [SMILES: *C1(*)OC1(*)*]

wherein each

independently represents a point of attachment to or within an organic compound or to a hydrogen atom.

The term "ester group" refers to a functional group, moiety, or substituent of an organic compound such that the organic compound has a carboxyl group

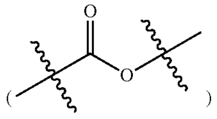 [SMILES: *OC(*)=O]

in either direction between two carbon atoms. Ester group substituents may have the general formula (IV) or (V):

(IV)

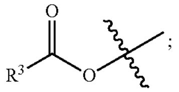

(V)

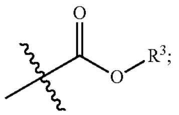

wherein $R^3$ is a straight-chain, branched, or cyclic ($C_1$-$C_{20}$) alkyl group, or an aryl, heteroaryl, or heterocyclic group; and

is the point of attachment of the ester group substituent to a carbon of the organic compound. Examples of ester group substituents may include an acrylate group:

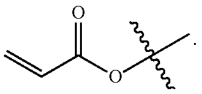

acrylate group

The term "amide group" refers to a functional group, moiety, or substituent of an organic compound such that the organic compound includes

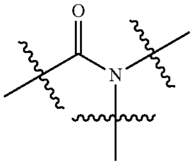 [SMILES: *C(=O)N(*)*]

in either direction, between carbon atoms, or between one or two hydrogen atoms and a carbon atom, or between a hydrogen atom and two carbon atoms. Amide group substituents may have the general formula (VI) or (VII):

(VI)

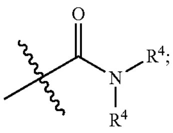

(VII)

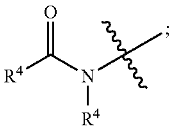

wherein each $R^4$ is independently hydrogen, or a straight-chain, branched, or cyclic ($C_1$-$C_{20}$)alkyl group, or an aryl, heteroaryl, or heterocyclic group; and

is the point of attachment of the amide group substituent to a carbon of the organic compound.

The term "frontal polymerization," refers, unless otherwise stated, to a process in which the polymerization reaction propagates through a vessel or a substance. There are three types of frontal polymerizations: thermal frontal polymerization ("TFP") that uses an external thermal energy source to initiate the front; photofrontal polymerization ("PFP"), in which the localized reaction is driven by an external UV source; and isothermal frontal polymerization ("IFP"), which relies on the Norrish-Trommsdorff, or gel effect, that occurs when monomer and initiator diffuse into a polymer seed (small piece of polymer). Thermal frontal polymerization begins when a heat source contacts a solution of monomer and a thermal initiator or catalyst. Alternatively, a UV source may be applied if a photoinitiator is also present. The area of contact (or UV exposure) has a faster polymerization rate, and the energy from the exothermic polymerization diffuses into the adjacent region, raising the temperature and increasing the reaction rate in that location. The result is a localized reaction zone that propagates down the reaction vessel as a thermal wave.

The term "ring-opening metathesis polymerization" ("ROMP"), refers, unless otherwise stated, to a type of olefin metathesis chain-growth polymerization that may produce industrially important products. The driving force of the reaction is relief of ring strain in cyclic olefins, which may be referred to as "functionalized cycloalkenes." Thus, "frontal ring-opening metathesis polymerization" ("FROMP") entails the conversion of a monomer into a polymer via a localized exothermic reaction zone that propagates through the coupling of thermal diffusion and Arrhenius reaction kinetics. The pot life, gel time, and reaction kinetics may be controlled through various modifications of the polymerization chemistry.

The term "pot life" refers to the amount of time between the mixing of monomer and initiator or catalyst and the point at which frontal polymerization is no longer possible. "Pot life" may also refer to the amount of time it takes for an initial viscosity of a composition to double, or quadruple. Timing starts from when the composition is mixed, and is measured at room temperature.

The term "rheological modifier" refers to a chemical species that may be added to a formulation or composition so as to alter the flow behavior or viscosity of the formulation or composition.

Herein is described a method to efficiently prepare oligomers of cycloalkenes via frontal ring-opening metathesis oligomerization ("FROMO") in which the average chain length and molecular weight distributions may be controlled by a molar ratio of cycloalkene to chain transfer agent. Whereas conventional syntheses of oligomers such as oligo-DCPD ("oDCPD") may involve high dilution with solvent, precluding application in large-scale syntheses, FROMO enables rapid synthesis of large quantities (for example, over 1 gram) of oligomers with minimal energy input and without the need for solvent.

Further, the resultant oligomeric products may act as rheological modifiers with cycloalkene monomers by forming a melt of the two components. The resultant monomer/oligomer melts may be liquids at ambient temperatures, which may provide significant advantages over existing FROMP resins. Moreover, the monomer/oligomer melts may achieve a range of viscosity, relevant to FROMP-based three-dimensional printing systems. The use of oligomer as a rheological modifier may enable direct chemical incorporation of the rheological modifier into the polymeric scaffold via cross-linking or chain transfer.

Further, the method described herein may enable a range of functionalities to be incorporated into FROMP polymers by selection of a chain end of an oligomer. By including appropriate chemical functionalities into an oligomer, multi-generational thermosets may be achieved by dynamic covalent chemistries, such as boronic ester exchange, or epoxide ring opening.

In an example, the present disclosure provides a method to prepare oligomers of a cycloalkene via a FROMO reaction including adding an amount of a phosphite ester and an amount of a catalyst to a cycloalkene and an amount of a chain transfer agent to provide a mixture, and heating the mixture to produce the oligomers. Average chain lengths and molecular weight distributions of oligomers prepared according to the method described herein may be controlled by a molar ratio of the amount of the cycloalkene to the amount of the chain transfer agent. In certain examples, the oligomers prepared according to the method described herein may be oligomers of formula (I):

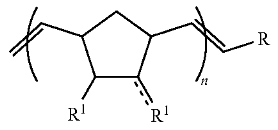

(I)

wherein R is a straight-chain, branched, or cyclic ($C_1$-$C_{20}$) alkyl group, or an aryl, heteroaryl, or heterocyclic group, wherein the ($C_1$-$C_{20}$)alkyl group or the aryl, heteroaryl, or heterocyclic group is optionally substituted with a boronate ester group, an epoxy group, a hydroxy group, an acrylate group, an ester group, or an amide group. Each $R^1$ may independently be hydrogen, a straight-chain, branched, or cyclic ($C_1$-$C_{20}$)alkyl group or ($C_1$-$C_{20}$)alkenyl group, and ═══ represents an optional double bond, wherein the $R^1$ at one end of the double bond is not a hydrogen. The two $R^1$ groups together may form a cycloalkyl or cycloalkenyl structure, together with the carbons to which the $R^1$ groups are attached. In other examples, one or both of the $R^1$ groups of one monomer may be different than one or both of the $R^1$ groups of an adjacent monomer in all or part of an oligomer, and two adjacent different monomers (in other words, "comonomers") together may form a repeating dimer. In other examples, the cycloalkene may be functionalized. Examples of functionalized cycloalkenes may include:

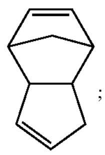

;

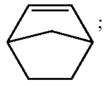

; and

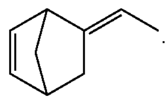

.

dicyclopentadiene norbornene 5-ethylidene-2-norbornene

In still other examples, the amount of the functionalized cycloalkane may be in a liquid phase. In still other examples, the chain transfer agent may be a monosubstituted olefin of formula (II):

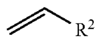

(II)

wherein $R^2$ is a straight-chain, branched, or cyclic ($C_1$-$C_{20}$) alkyl group or ($C_1$-$C_{20}$)alkoxy group, or an aryl, heteroaryl, or heterocyclic group, optionally substituted with a halogen atom, a hydroxy group, a boronate ester group, an epoxy group, an acrylate group, an ester group, or an amide group.

Examples of Chain Transfer Agents May Include:

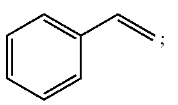
styrene

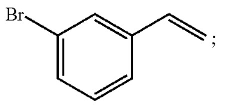
3-bromostyrene

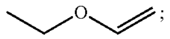
ethyl vinyl ether and

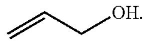
prop-2-en-1-ol

In still other examples, the molar ratio of the amount of the functionalized cycloalkene to the amount of the chain transfer agent may be from about 1:1 to about 50:1, including from about 2:1, or from about 3:1, or from about 4:1, or from about 5:1, or from about 6:1, or from about 7:1, or from about 8:1, or from about 9:1, or from about 10:1, or from about 15:1, or from about 20:1, or from about 25:1, or from about 30:1, or from about 35:1, or from about 40:1, or from about 45:1; or to about 2:1, or to about 3:1, or to about 4:1, or to about 5:1, or to about 6:1, or to about 7:1, or to about 8:1, or to about 9:1, or to about 10:1, or to about 15:1, or to about 20:1, or to about 25:1, or to about 30:1, or to about 35:1, or to about 40:1, or to about 45:1; including any range made from any two of the foregoing ratios; and including any sub-ratios therebetween.

In still other examples, an amount of a phosphite ester may be added to the amount of the functionalized cycloalkene and the amount of the chain transfer agent. The phosphite ester may be of a formula $P(OR^3)_3$, wherein $R^3$ are all simultaneously or each independently methyl, ethyl, n-butyl, tert-butyl, or phenyl.

In still other examples, an amount of a catalyst may be added to the amount of the functionalized cycloalkene and the amount of the chain transfer agent. In still other examples, a molar ratio of the amount of the catalyst to the amount of the functionalized cycloalkene may be less than about 1:100, or less than about 1:200, or less than about 1:300, or less than about 1:400, or less than about 1:500, or less than about 1:600, or less than about 1:700, or less than about 1:800, or less than about 1:900, or less than about 1:1000, or less than about 1:2000, or less than about 1:3000, or less than about 1:4000, or less than about 1:5000, or less than about 1:6000, or less than about 1:7000, or less than about 1:8000, or less than about 1:9000, or less than about 1:10000; or a range made from any of the two foregoing ratios; and including any sub-ratios therebetween.

In still other examples, the catalyst may be a Grubbs catalyst. Examples of Grubbs catalysts may include G2:

G2

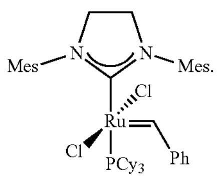

In still other examples, heating the mixture may include applying a heat source to the mixture at a temperature of from about 50 to about 500° C., including, for example, from about 75° C., or from about 100° C., or from about 125° C., or from about 150° C., or from about 175° C., or from about 200° C., or from about 225° C., or from about 250° C., or from about 275° C., or from about 300° C., or from about 325° C., or from about 350° C., or from about 375° C., or from about 400° C., or from about 425° C., or from about 450° C., or from about 475° C.; or to about 75° C., or to about 100° C., or to about 125° C., or to about 150° C., or to about 175° C., or to about 200° C., or to about 225° C., or to about 250° C., or to about 275° C., or to about 300° C., or to about 325° C., or to about 350° C., or to about 375° C., or to about 400° C., or to about 425° C., or to about 450° C., or to about 475° C.; or any range of temperatures made from any two of the foregoing temperatures; including any sub-ranges therebetween.

In still other examples, a degree of polymerization for oligomers prepared according to the methods described herein may be an average degree of polymerization. In still other examples, a degree or average degree of polymerization may be a number-average degree of polymerization of from 3 to 30, including, for example, from 4, or from 5, or from 6, or from 7, or from 8, or from 9, or from 10, or from 11, or from 12, or from 13, or from 14, or from 15, or from 16, or from 17, or from 18, or from 19, or from 20, or from 21, or from 22, or from 23, or from 24, or from 25, or from 26, or from 27, or from 28, or from 29; or to 4, or to 5, or to 6, or to 7, or to 8, or to 9, or to 10, or to 11, or to 12, or to 13, or to 14, or to 15, or to 16, or to 17, or to 18, or to 19, or to 20, or to 21, or to 22, or to 23, or to 24, or to 25, or to 26, or to 27, or to 28, or to 29; or a range made from any two of the foregoing numbers; including any sub-ranges therebetween.

In still other examples, when a molar ratio of the amount of the functionalized cycloalkene to the amount of the chain transfer agent is about 5:1, an average degree of polymerization of the oligomers produced by the method may be 5. In still other examples, when a molar ratio of the amount of the functionalized cycloalkene to the amount of the chain transfer agent is about 35:1, an average degree of polymerization of the oligomers produced by the method may be 28.

In an example, the present disclosure provides a method of preparing a polymer via a FROMP reaction from a second amount of the functionalized cycloalkene and the oligomers prepared by a method described herein, including adding the oligomers and the second amount of the functionalized cycloalkene or a mixture of functionalized cycloalkenes to a second amount of a phosphite ester and a second amount of a catalyst to provide a second mixture, and heating the second mixture to produce the polymer. In certain examples, the oligomers may be of formula (I).

In certain examples, the second amount of the functionalized cycloalkene and the oligomers may be a melt having a viscosity at ambient temperature of less than about 20 Pa·s, including less than about 19 Pa·s, or less than about 18 Pa·s, or less than about 17 Pa·s, or less than about 16 Pa·s, or less than about 15 Pa·s, or less than about 14 Pa·s, or less than about 13 Pa·s, or less than about 12 Pa·s, or less than about 11 Pa·s, or less than about 10 Pa·s, or less than about 9 Pa·s, or less than about 8 Pa·s, or less than about 7 Pa·s, or less than about 6 Pa·s, or less than about 5 Pa·s, or less than about 4 Pa·s, or less than about 3 Pa·s, or less than about 2 Pa·s, or less than about 1 Pa·s; or greater than about 1 Pa·s, or greater than about 2 Pa·s, or greater than about 3 Pa·s, or greater than about 4 Pa·s, or greater than about 5 Pa·s, or greater than about 6 Pa·s, or greater than about 7 Pa·s, or greater than about 8 Pa·s, or greater than about 9 Pa·s, or greater than about 10 Pa·s, or greater than about 11 Pa·s, or greater than about 12 Pa·s, or greater than about 13 Pa·s, or greater than about 14 Pa·s, or greater than about 15 Pa·s, or greater than about 16 Pa·s, or greater than about 17 Pa·s, or greater than about 18 Pa·s, or greater than about 19 Pa·s, or greater than about 20 Pa·s; or a viscosity in a range made from any two of the foregoing numbers; including any sub-ranges therebetween.

In other examples, a method of preparing a polymer described herein may be free of solvent.

In still other examples, oligomers of formula (I) may be in an amount of from about 20 weight % to about 80 weight % based on a combined weight % of oligomers of formula (I) and functionalized cycloalkene, including, for example, from about 25 weight %, or from about 30 weight %, or from about 35 weight %, or from about 40 weight %, or from about 45 weight %, or from about 50 weight %, or from about 55 weight %, or from about 60 weight %, or from about 65 weight %, or from about 70 weight %, or from about 75 weight %; or to about 25%, or to about 30 weight %, or to about 35 weight %, or to about 40 weight %, or to about 45 weight %, or to about 50 weight %, or to about 55 weight %, or to about 60 weight %, or to about 65 weight %, or to about 70 weight %, or to about 75 weight %; or a range made from any two of the foregoing weight percentages, including any sub-ranges therebetween.

In still other examples, a polymer prepared by a method described herein may have a glass transition temperature of about 140° C., as measured by differential scanning calorimetry.

Scheme A below illustrates an example of competitive, or tandem, catalytic cycles for a FROMO reaction of DCPD with styrene as a chain transfer agent. According to Scheme A, oligo-DCPD is propagated at a propagation reaction rate with rate constant $k_p$, and propagation, and consequently, number-average degree of polymerization, depends on the molar ratio of DCPD to styrene. The higher the molar ratio of DCPD relative to styrene, the greater the extent of propagation, and the greater the number-average degree of polymerization. The lower the molar ratio of DCPD relative to styrene, the more that styrene may compete with DCPD. According to Scheme A, styrene undergoes a cross-metathesis reaction to terminate propagation, at a termination reaction rate with a rate constant $k_t$. The rate constants $k_p$ and $k_t$ are comparable, so the propagation and termination reactions are competitive. Therefore, the degree of polymerization of oligo-DCPD is controllable based on relative molar amounts of DCPD and styrene used in the reaction.

Scheme A

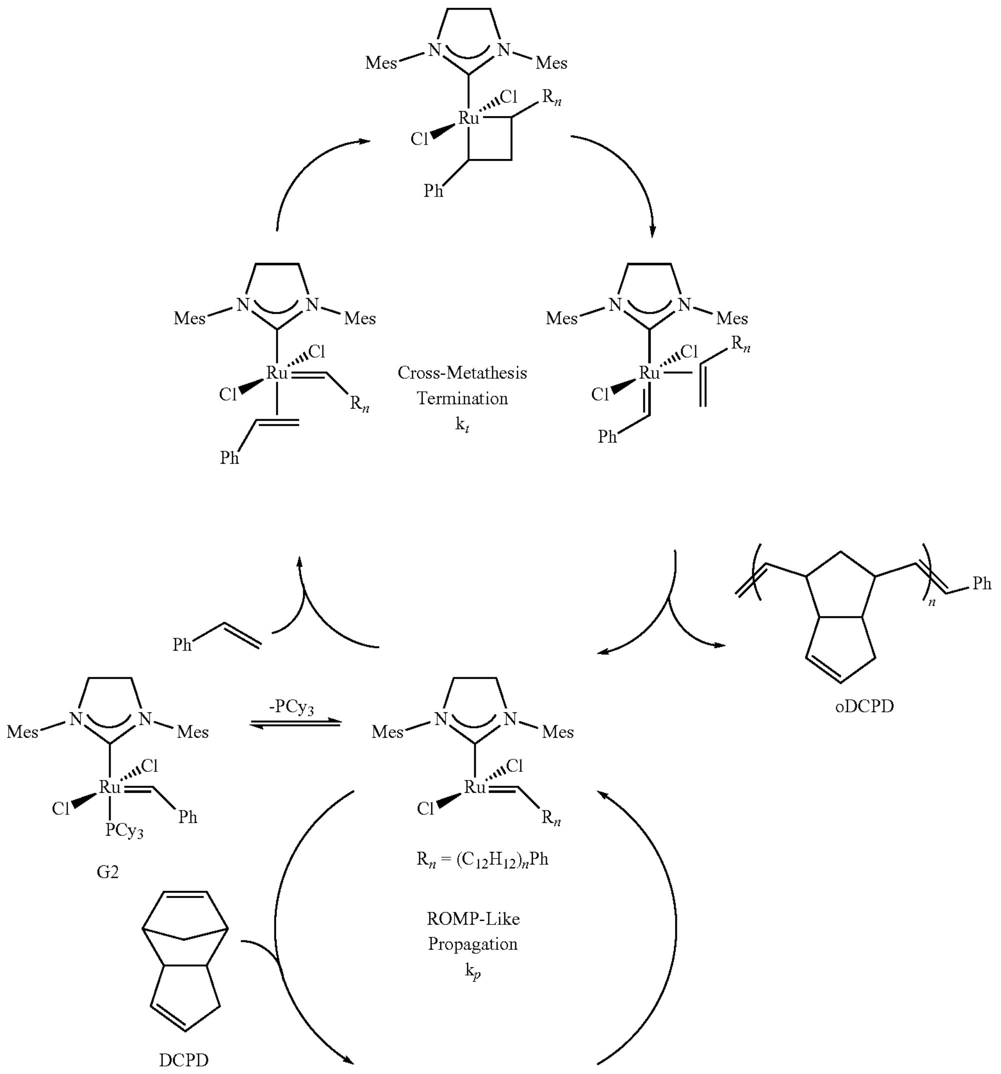

-continued

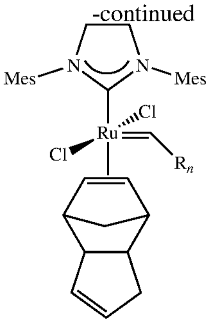

The compositions and methods described above may be better understood in connection with the following Examples. In addition, the following non-limiting examples are an illustration. The illustrated methods are applicable to other examples of oligomers of formula (I) or other chain transfer agents of formula (II) of the present disclosure. The procedures described as general methods describe what is believed will be typically effective to prepare the compositions indicated. However, the person skilled in the art will appreciate that it may be necessary to vary the procedures for any given example of the present disclosure, for example, vary the order or steps and/or the chemical reagents used.

EXAMPLES

I. Materials

All reactions and experiments, unless otherwise noted, were performed under an ambient atmosphere. Dicyclopentadiene ("DCPD,"≥96%), 5-ethylidene-2-norbornene (ENB, 99%), norbornene (NBE, 98%), styrene (≥99%), 3-bromostyrene (95%), ethyl vinyl ether ("EVE," >99%), dichloromethane ("DCM,"≥99.8%), methanol (99.8%), tributyl phosphate ($P(O^nBu)_3$, "TBP," 95%), second generation Grubbs catalyst, ([(SIMes)Ru(=CHPh)($PCy_3$)$Cl_2$], "G2"), and phenylcyclohexane (≥97%) were purchased from Sigma-Aldrich and used without further purification.

II. Characterization

A. Spectrometry and Spectroscopy

All $^1$H and $^{13}$C NMR experiments were carried out using a Varian VXR-500 FT-NMR spectrometer equipped with a 5 mm Nalorac Quad probe or on a 500 MHz Bruker Avance III HD NMR spectrometer equipped with a 60-position SampleXpress autosampler and a multi-nuclear liquid nitrogen-cooled CryoProbe. FT-IR spectra were acquired on a Perkin Elmer Spectrum. One spectrometer equipped with a DuraSamplIR ATR diamond crystal. Powder X-ray diffraction experiments were performed on a Rigaku Miniflex 600 powder X-ray diffraction system, a benchtop PXRD instrument optimized to collect data in a 2θ scan range of 3° to 120° in reflection mode, with a Cu source (600 W, 40 kV-15 mA).

B. $^1$H NMR End-Group Analysis

The molecular weights of o(DCPD), oligo-5-ethylidene-2-norbornene ("o(ENB)"), and oligo-norbornene ("o(NBE)") were measured by $^1$H-end group analysis in THF-$d_8$ or chloroform-d on a 500 MHz NMR spectrometer. The tabulated results are provided in Table 8.

The degree of polymerization for o(DCPD) (in other words, the number of repeating units; $\overline{\chi_{0(DCPD)}}$) was determined using as end-group the integral (I) of the signals between 7.50 and 7.00 (5H) and the backbone integral (I) between 3.02 and 2.75 (3H), using the following equation (1):

$$\overline{X_{o(DCPD)}} = \frac{I(3.02 - 2.75)/3}{I(7.50 - 7.02)/5}. \quad (1)$$

The number-average molecular weight ($\overline{M}_0$(DCPD)) was determined using the following equation (2):

$$\overline{M}_{o(DCPD)} = (\overline{X_{o(DCPD)}} * 132) + 104. \quad (2)$$

The degree of polymerization for o(ENB) was determined using as end-group the integral (I) of the signals between 7.50 and 7.00 (5H) and the backbone integral (I) signal between 5.50 and 5.00 (3), using the following equation (3):

$$\overline{X_{o(ENB)}} = \frac{I(5.50 - 5.00)/3}{I(7.50 - 7.00)/5}. \quad (3)$$

The number-average molecular weight ($\overline{M}_0$(ENB)) was determined using the following equation (4):

$$\overline{M}_{o(ENB)} = (\overline{X_{o(ENB)}} * 120) + 104. \quad (4)$$

The degree of polymerization for o(NBE) was determined using as end-group the integral (I) of the signals between 7.50 and 7.00 (5H) and the backbone integral (I) signal between 5.40 and 5.10 (2H), using the following equation (5):

$$\overline{X_{o(NBE)}} = \frac{I(5.40 - 5.10)/2}{I(7.50 - 7.00)/5}. \quad (5)$$

The number-average molecular weight ($\overline{M}_0$(NBE)) was determined using the following equation (6):

$$\overline{M}_{o(NBE)} = (\overline{X_{o(NBE)}} * 94) + 104. \quad (5)$$

The complexity and distribution of chain ends present among the oligomers of formula (I) tested introduces error into the $\overline{M}_n$. The values derived from $^1$H NMR end-group analysis, therefore, provide qualitative $\overline{M}_n$ rather than absolute values. The observed trend of [styrene]$_0$ on $\overline{M}_n$, however, is likely reliable, because any error is consistent among various samples tested.

C. Differential Scanning Calorimetry: Oligomer Post-Cure

Figure 4:
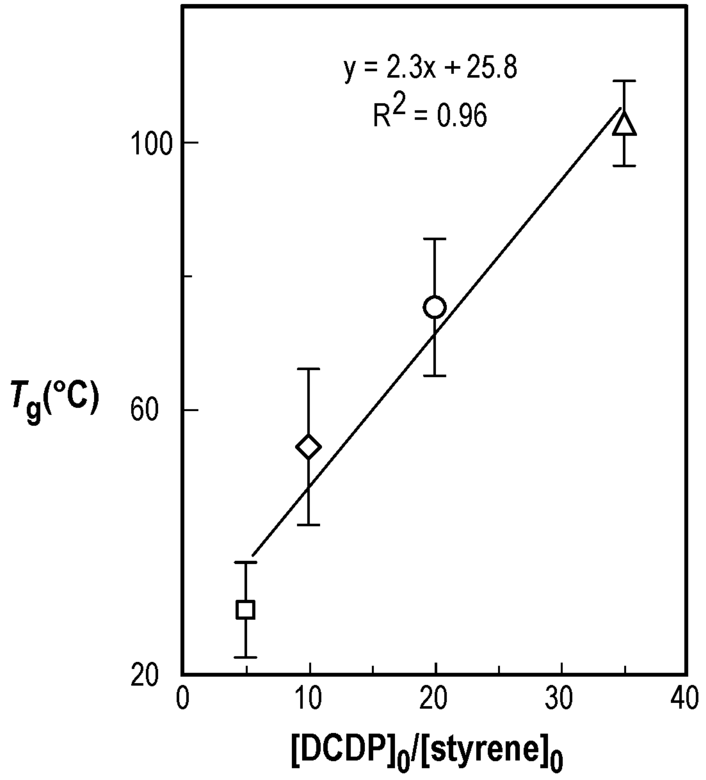
FIG. 4 illustrates o(DCPD) glass transition temperatures ($T_g$) as a function of DCPD to styrene molar ratios, the $T_g$ values measured by DSC.
Figure 5A:
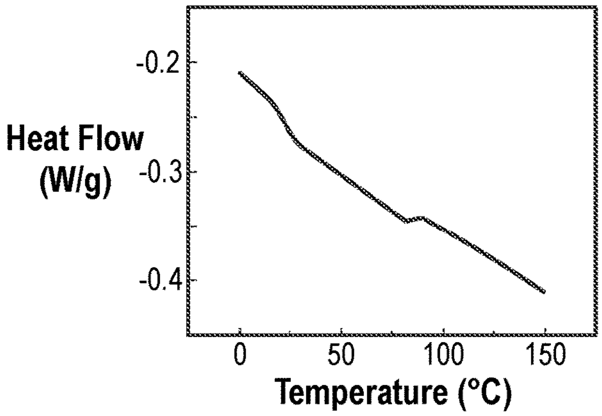
FIG. 5A illustrates a DSC thermograph of synthesized o(DCPD) at a DCPD to styrene molar ratio of 5:1 (Formulation 1)
Figure 5B:
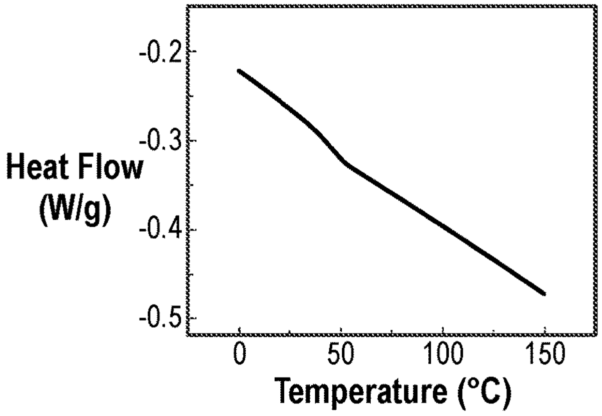
FIG. 5B illustrates a DSC thermograph of synthesized o(DCPD) at a DCPD to styrene molar ratio of 10:1 (Formulation 2)
Figure 5C:
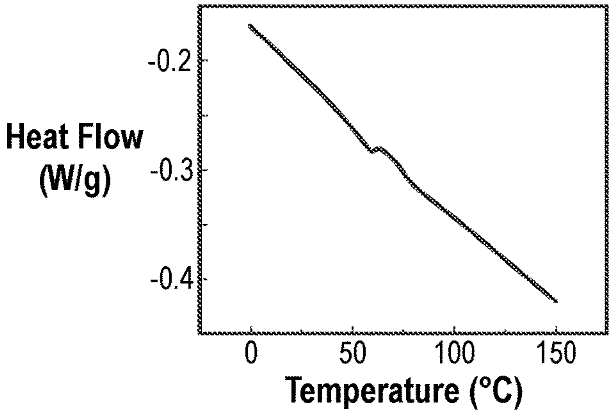
FIG. 5C illustrates a DSC thermograph of synthesized o(DCPD) at a DCPD to styrene molar ratio of 20:1 (Formulation 3)
Figure 5D:
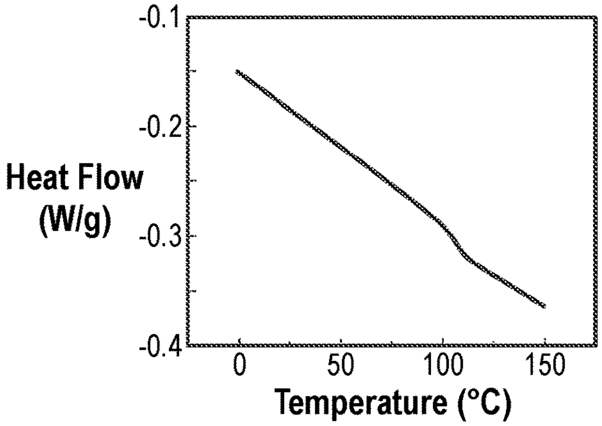
FIG. 5D illustrates a DSC thermograph of synthesized o(DCPD) at a DCPD to styrene molar ratio of 35:1 (Formulation 4)

Differential scanning calorimetry ("DSC") experiments were performed on a TA Discovery DSC 250 instrument. Cured o(DCPD) samples obtained from reactions of mixture numbers 1-4 were transferred into aluminum hermetic DSC pans at room temperature, and sealed. The sample mass was determined using an analytical balance (XPE205, Mettler-Toledo) and carefully maintained between 5 milligrams and 10 milligrams. The specific heat capacity was determined by comparison to a sapphire standard. Each sample was subjected to three thermal cycles (heat, cool, and second heat). Samples were subjected to a first heating ramp from −50 to 200° C. at a rate of 15° C.·min$^{-1}$, and subsequently cooled to −50 at a rate of 15° C.·min$^{-1}$. The second heat scan occurred at a ramp rate of 5° C.·min$^{-1}$ over the same temperature range. The glass transition temperatures ($T_g$) were determined from the midpoint of the thermal transition observed in the second heat scan. The $T_g$ data is summarized in Table 8 and illustrated in FIG. 4. Post-cure DSC traces are illustrated in FIGS. 5A-5D.

The DSC curves demonstrated differences in the thermochemical properties of o(DCPD as a function of the substrate composition, as illustrated in FIGS. 5A-5D. The o(DCPD) samples were amorphous materials, as confirmed by powder X-ray diffraction experiments, and undergo glass-transitions at temperatures ($T_g$) far lower than the temperatures typically associated with glass-transition temperatures of FROMP products (approximately 160 to 250° C.). Indeed, the oligomers demonstrate fluid-flow behavior during the FROMO process. The $T_g$ values of the oligomers indirectly scale with styrene content with regard to changes in $\overline{M}_n$. Short-chain oligomers at a DCPD:styrene molar ratio of 5:1 exhibited $T_g$ values of 30°±7° C., whereas oligomers at a DCPD:styrene molar ratio of 35:1 exhibited $T_g$ values of 103°±6° C.

D. Size Exclusion Chromatography ("SEC")

Size exclusion chromatography was performed on an Agilent 1260 Infinity system equipped with an isocratic pump, degasser, autosampler, and a series of 4 Waters HR Styragel columns (7.8×300 mm, HR1, HR3, HR4, and HR5) in THF at 25° C. and a flow rate of 1 mL·min$^{-1}$. The system was equipped with a triple detection system that includes an Agilent 1200 series G1362A Infinity Refractive Index Detector ("RID"), a Wyatt Viscostar II viscometer detector, and a Wyatt MiniDAWN Treos 3-angle light-scattering detector. Molecular weights ($\overline{M}_w$ and $\overline{M}_n$) and dispersities (Đ) were determined by a 12-point conventional column calibration with narrow dispersity polystyrene ("PS") standards ranging from 980 to 1,013,000 Da. The error in the absolute values measured in SEC may vary substantially, because the calibration assumes that o(DCPD) behaves similarly to PS (the error in the measurement is ±10.7%). Trends in molecular weight are generally considered to be reliable with this type of calibration. Representative SEC traces are illustrated in FIGS. 3, 12, 15, and 19 and the data is summarized in Table 8.

E. Matrix Assisted Laser Desorption Ionization Time of Flight ("MALDI-TOF")

Oligomer (10 mg·mL$^{-1}$), trans-2-[3-(4-tert-Butylphenyl)-2-methyl-2-propenylidene]malononitrile ("DCTB") (20 mg·mL$^{-1}$), and AgTFA (1 mg·mL$^{-1}$) were independently dissolved in THF. Then, 10 μL of oligomer, 30 μL of DCTB, and 1 μL of AgTFA were mixed to form a solution. Finally, 5 μL of the solution was spotted in a MALDI plate and analyzed with a Bruker Daltonics UltrafleXtreme MALDI TOFTOF instrument. All species were ionized as $Ag^+$ adducts. Mass-spectral peaks were picked using the FlexAnalysis software package. The automatic peak-picking algorithm method determined the centroid of the low-resolution MALDI peaks with a signal-to-noise ratio of at least 10 and peak-widths of at least 4 m/z units. The peak-picked MALDI values were used for subsequent analyses. The number average molecular weight ($\overline{M}_n$) was calculated from the MALDI-TOF intensity ($N_i$) and the molecular weight ($M_i$) as $Ag^+$ (+107.9 m/z) adducts according to the following equation (7):

$$\overline{M}_n = \frac{\Sigma N_i \times M_i}{\Sigma N_i}. \quad (7)$$

The weight average molecular weight ($\overline{M}_w$) was calculated according to the following equation (8):

$$\overline{M}_w = \frac{\Sigma N_i \times M_i^2}{\Sigma N_i \times M_i}. \quad (8)$$

Finally, dispersity (Đ) was calculated as the ratio $\overline{M}_w/\overline{M}_n$. Full MALDI traces are illustrated in FIGS. 2A-2D. 9, 11A-11D, 14A-14B, 18A-18B, 21, and 23 and the data is summarized in Table 8.

The derivation of $\overline{M}_w$ and $\overline{M}_n$ by MALDI relies on several assumptions and approximations. First, the identification of species requires that a sufficient concentration of analyte reach the MS-detector. The probability of detection is governed by the concentration of the analyte within the bulk sample and the propensity for ionization. It is assumed that all oligomer species ionize to the same degree and that the MS-intensity results only from the bulk concentration, but the assumption does not hold true over a large m/z range or with oligomers bearing vastly different functionalities. Second, a typical MALDI experiment only records species with m/z in the range of ≈0.6 to 10 kDa. Therefore, MALDI tends to overestimate oligomer molecular weights. Despite the above assumptions and approximations, the observed trend of [styrene]$_0$ on $\overline{M}_n$ is reliable as this error is consistent across the samples tested. The absolute values must be considered with caution.

F. Kendrick Mass-Analysis

Kendrick mass-analyses of the MALDI data exploits mass referencing. The first step in Kendrick mass-analysis involves re-referencing the peak-picked MALDI spectrum. The International Union of Pure and Applied Chemistry ("IUPAC") system indexes all atomic masses relative to $^{12}C$ (12.0000 Da). Any fractional values, therefore, occur as the result of atom types other than $^{12}C$. For small-molecule organics, Kendrick mass-analysis proposes that methylene ($^{12}C_1H_2$; IUPAC m/z=14.0157 Da) provides a better referencing point. In the new Kendrick mass scale, the monoisotopic mass of methylene is redefined as 14.0000, and all other masses are adjusted by the ratio of the two masses (in other words, 14.0000/14.0157). All non-integer values in the new mass scale arise from fragments other than $^{12}C^1H_2$. Thereby, Kendrick mass-analysis enables the generation of a second dimension for analysis, which differentiates species of different masses.

For high-resolution data sets, each individual isotopomer is detectable. In such data sets, the fractional mass difference may provide a useful second dimension for discrimination. Fractional masses are rounded to the nearest whole number. By contrast, low-resolution or linear-mode MALDI spectra exhibit worse m/z resolutions but often may provide significantly better signal-to-noise ratios. Detected masses, therefore, appear as broadened peaks rather than an ensemble of individual isotopomers. The maximum of the broadened peaks corresponds to the molecular weight of the species rather than the monoisotopic mass. In such cases, the fractional mass cannot be used. Instead, the remainder of the Kendrick mass ("RKM") provides information related to fragments other than the IUPAC mass of the repeat unit. For the oligomers described in this work, the remainder mass corresponds to the mass of the chain-ends.

Figure 20A:
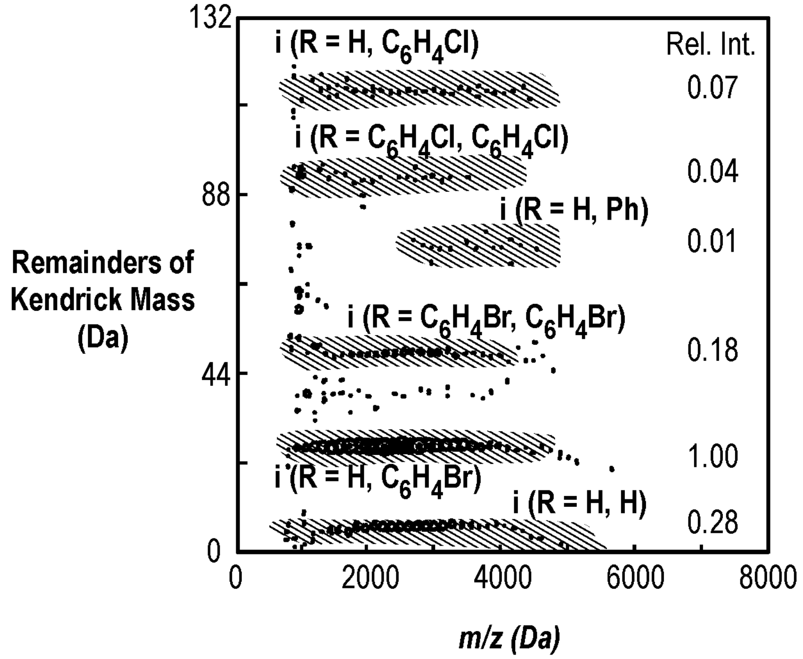
FIG. 20A illustrates Kendrick mass-analysis of o(DCPD) terminated with 3-bromostyrene (Formulation 13) as the added CTA.
Figure 20B:
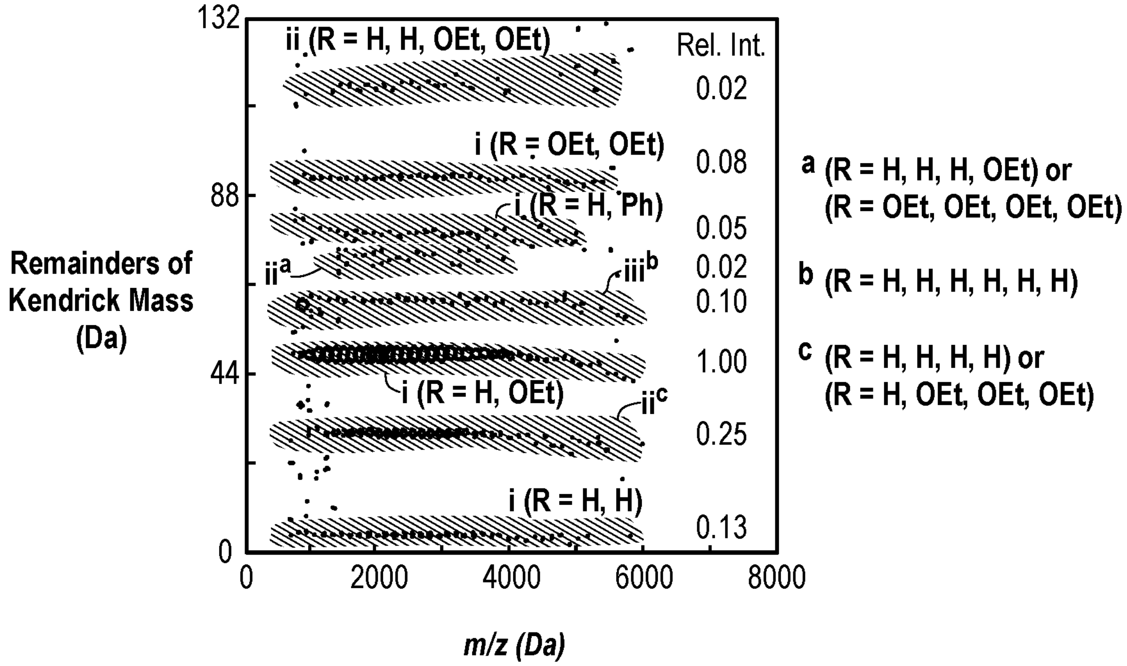
FIG. 20B illustrates Kendrick mass-analysis of o(DCPD) terminated with EVE as the added CTA.

Kendrick-mass analysis of FROMO products derived from chain transfer agents (3-bromostyrene, EVE) are illustrated in FIGS. 20A and 20B respectively. Remainder Kendrick plots are constructed by plotting the RKM as a function of the measured m/z value. Species with identical chain-ends (and adducting ions) align horizontally in the remainder Kendrick plots at a single remainder value.

For species with masses greater than 2 kDa, the difference between a monoisotopic mass and the molecular weight of a species may become non-trivial. For example, an oligomer with 20 DCPD units (ignoring chain-ends and $Ag^+$ ions), has a monoisotopic mass of 2641.8780 and a molecular weight of 2644.1200 in IUPAC standards. Because the peak maxima in low-resolution MALDI spectra correspond to the molecular weight rather than the monoisotopic mass, the difference between the two values must be considered (Δ m/z=2.2420 Da). In the Kendrick remainder plots illustrated in the figures, the horizontally aligned species may drift over a 6 kDa range by as much as 4 Da.

III. Syntheses

A. General Synthesis of o(DCPD)

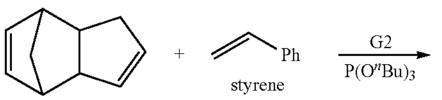

DCPD styrene

-continued

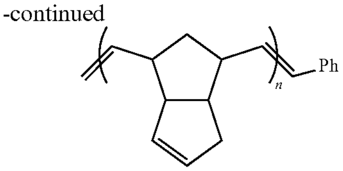

o(DCPD)

Figure 1B:
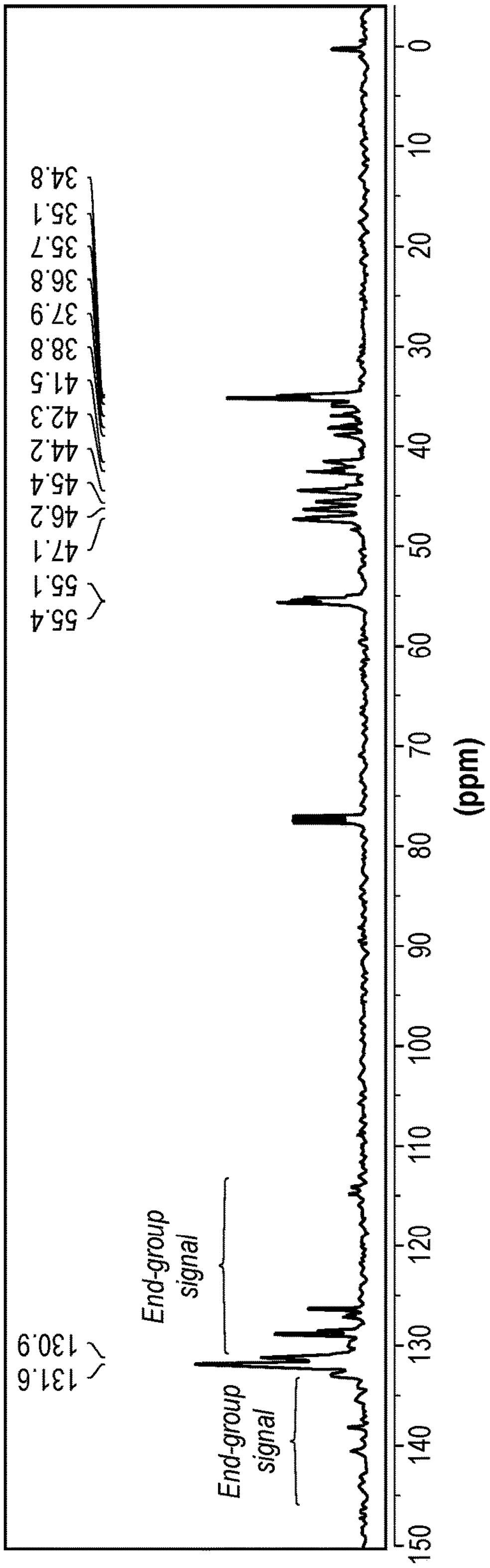
FIG. 1B illustrates a $^{13}C\{^{1}H\}$ spectrum (126 MHz, chloroform-d with 1% v/v $SiMe_4$) of o(DCPD) derived from Formulation 1.
Figure 2A:
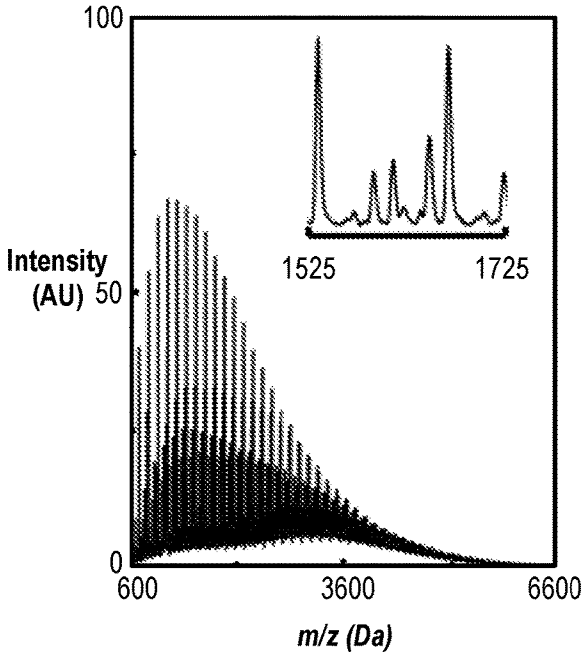
FIG. 2A illustrates a MALDI-TOF mass spectrum for o(DCPD) terminated with styrene at a molar ratio of DCPD to styrene of 5:1 (Formulation 1)
Figure 2B:
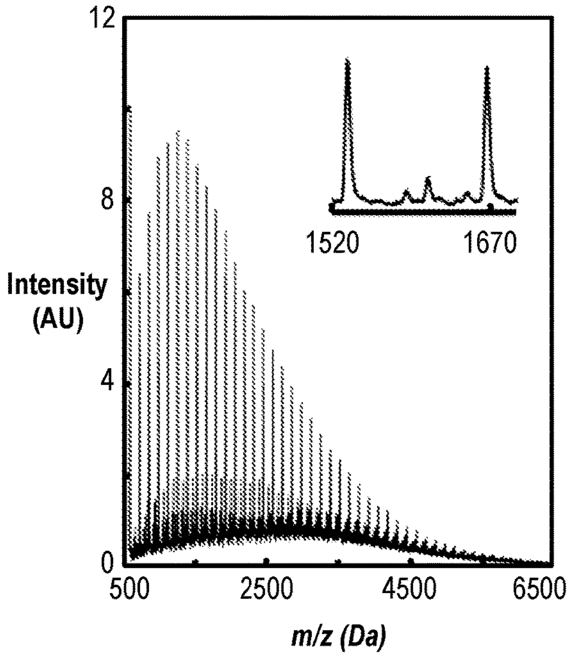
FIG. 2B illustrates a MALDI-TOF mass spectrum for o(DCPD) terminated with styrene at a molar ratio of DCPD to styrene of 10:1 (Formulation 2)
Figure 2C:
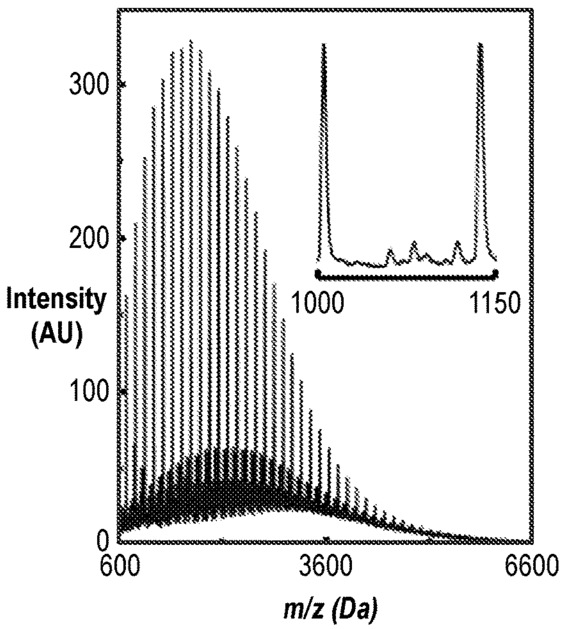
FIG. 2C illustrates a MALDI-TOF mass spectrum for o(DCPD) terminated with styrene at a molar ratio of DCPD to styrene of 20:1 (Formulation 3)
Figure 2D:
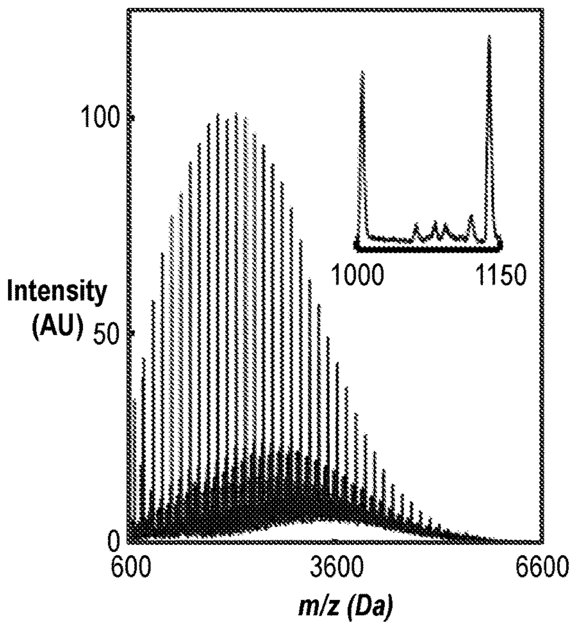
FIG. 2D illustrates a MALDI-TOF mass spectrum for o(DCPD) terminated with styrene at a molar ratio of DCPD to styrene of 35:1 (Formulation 4)
Figure 3:
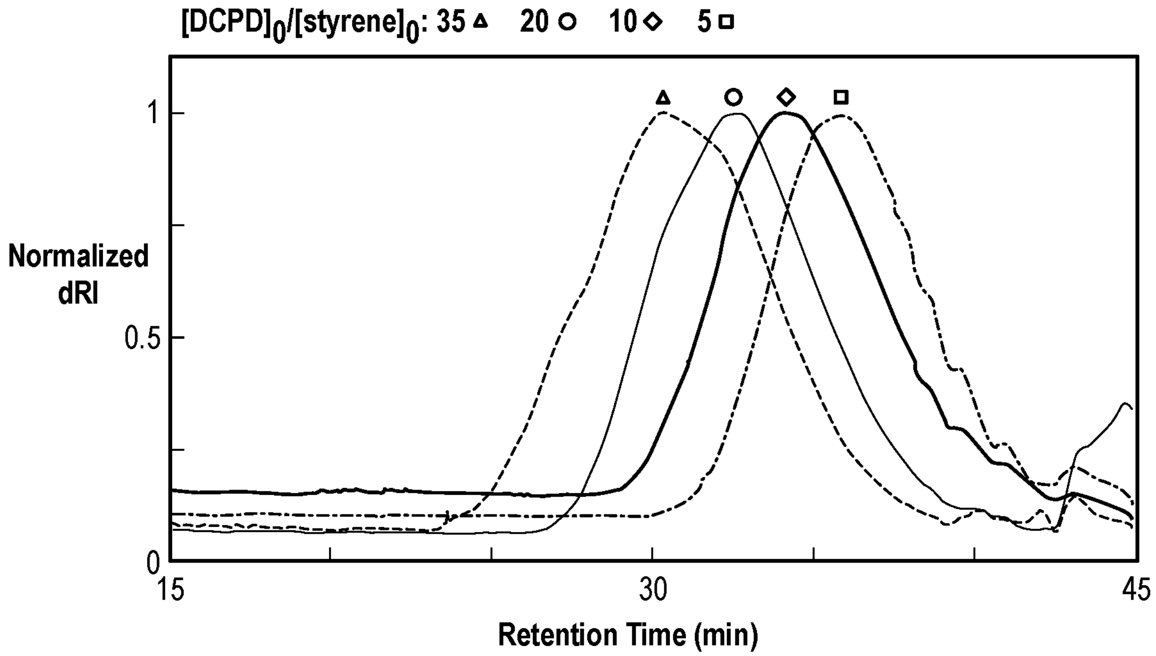
FIG. 3 illustrates size-exclusion chromatograms of o(DCPD) at various DPCD to styrene molar ratios.

Solvent-free resins employed for frontal oligomerization were prepared with the following exemplary procedure for formulation composition 1. Specific formulation compositions, including formulation composition 1, are found in Table 1 below. For formulation 1: DCPD (25.0 g, 189 mmol, 5 equiv.), styrene (4.4 mL, 38 mmol, 1 equiv.), $P(O^nBu)_3$ (4.2 μL, 16 μmol, 0.52, mM), and G2 (13 mg, 15 μmol, 0.51 mM). Solid DCPD was liquefied with styrene (2.2 mL), and subsequently a solution of G2 and $P(O^nBu)_3$ in styrene (2.2 mL) was added to the monomer solution to afford the oligomerization resin. This resin was added to a 25×150 mm glass test tube, and frontal ring-opening metathesis oligomerization (FROMO) was initiated by touching a hot soldering iron to the glass at the liquid-to-air interface. The oligomer produced by the FROMO reaction was dissolved in dichloromethane (50 mL) and was then precipitated from solution with the addition of methanol (100 mL) to afford a stick white solid. The solid was washed twice with additional methanol (100 mL) to provide oligo-dicyclopentadiene (o(DCPD)) as a white solid. Volatile components were removed under reduced pressure over 16 h. The material was crushed into a fine white powder (18.0 g, 62% mass recovery). Full NMR spectra are illustrated in FIGS. 1A and 1B. Representative MALDI-TOF traces are illustrated in FIGS. 2A-2D. Representative SEC traces are illustrated in FIG. 3. Tabulated molecular weight data from end-group analysis, MALDI, and SEC are provided in Table 8. Thermochemical data from DSC are provided in Table 8 and illustrated in FIGS. 4 and 5A-5D.

TABLE 1

Composition of resin solutions with various DCPD-to-styrene molar ratios at fixed amounts of G2 (13 mg, 15 μmol) and $P(O^nBu)_3$ (4.2 μL, 16 μmol)

| Formulation Number | DCPD/styrene mol/mol ratio | DCPD (g) | Styrene (mL) | Mass Recovery (g) | Mass Yield (%) |
|---|---|---|---|---|---|
| 1 | 5:1 | 25.0 | 4.4 | 18.0 | 62 |
| 2 | 10:1 | 29.4 | 2.6 | 25.9 | 81 |
| 3 | 20:1 | 29.4 | 1.3 | 27.8 | 91 |
| 4 | 35:1 | 29.4 | 0.8 | 29.7 | >95 |
| 5[a] | 12:1 | 117.6 | 8.7 | 119.9 | >95 |
| 6[b] | 34 | 117.6 | 3.0 | 95.5 | 79 |

[a]G2 (43 mg, 51 μmol) and $P(O^nBu)_3$ (14 μL, 51 μmol);
[b]G2 (52 mg, 61 μmol) and $P(O^nBu)_3$ (17 μL, 62 μmol).

Figure 6:
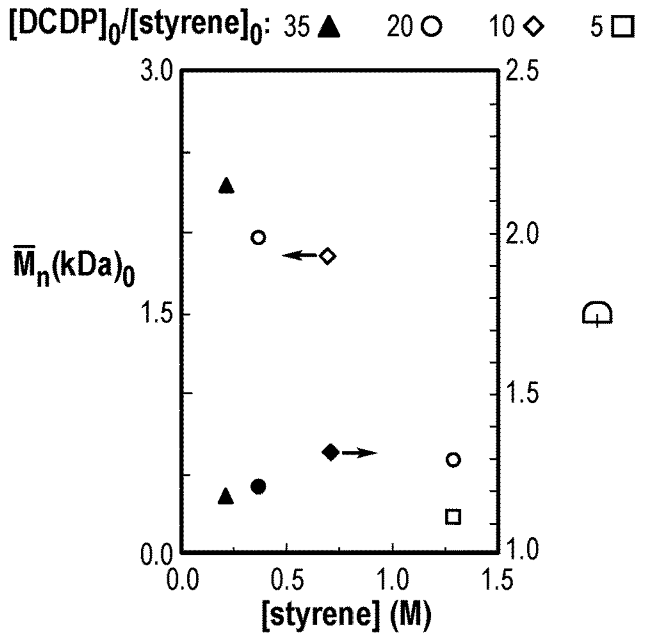
FIG. 6 illustrates number-average molecular weights ($\overline{M}_n$, unfilled) and dispersities (Đ, filled) as a function of styrene concentration in neat DCPD.
Figure 7:
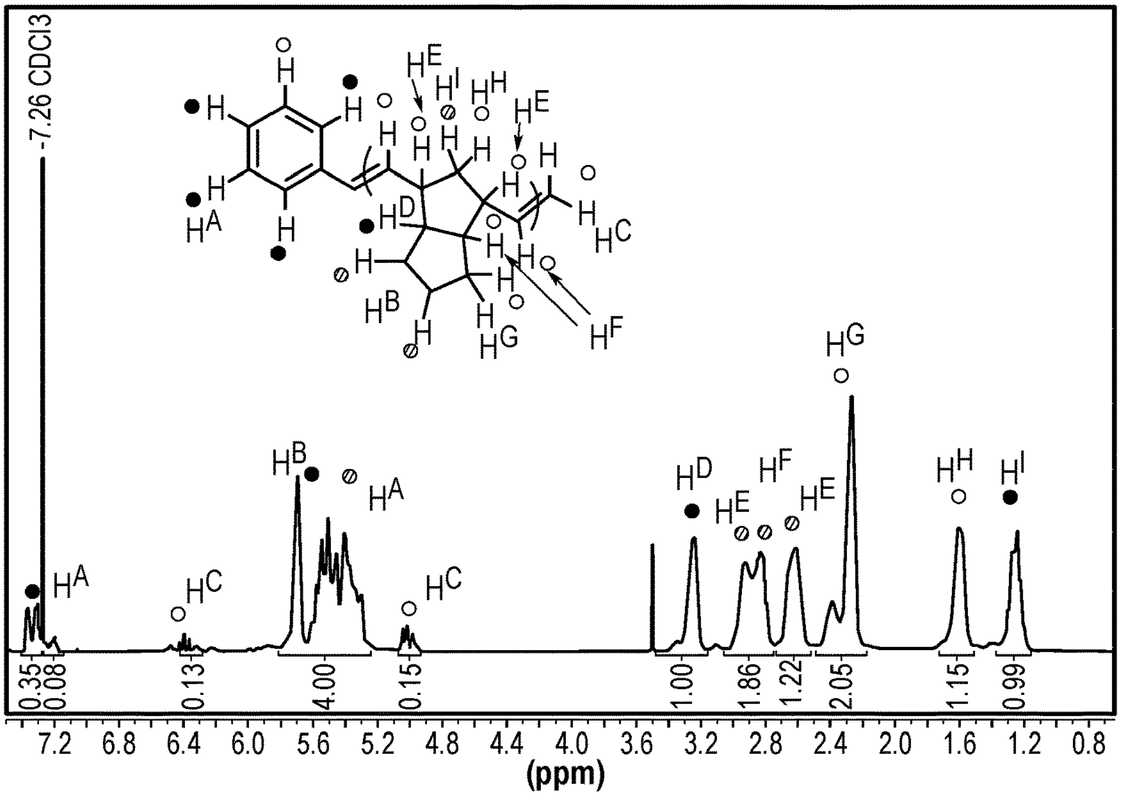
FIG. 7 illustrates a $^{1}$H NMR spectrum in chloroform-d of o(DCPD) prepared with a 10:1 ratio of DCPD to styrene, with an average $\chi_n$ of 6.5 ($M_w$=0.9 kDa) determined by chain end analysis.
Figure 8:
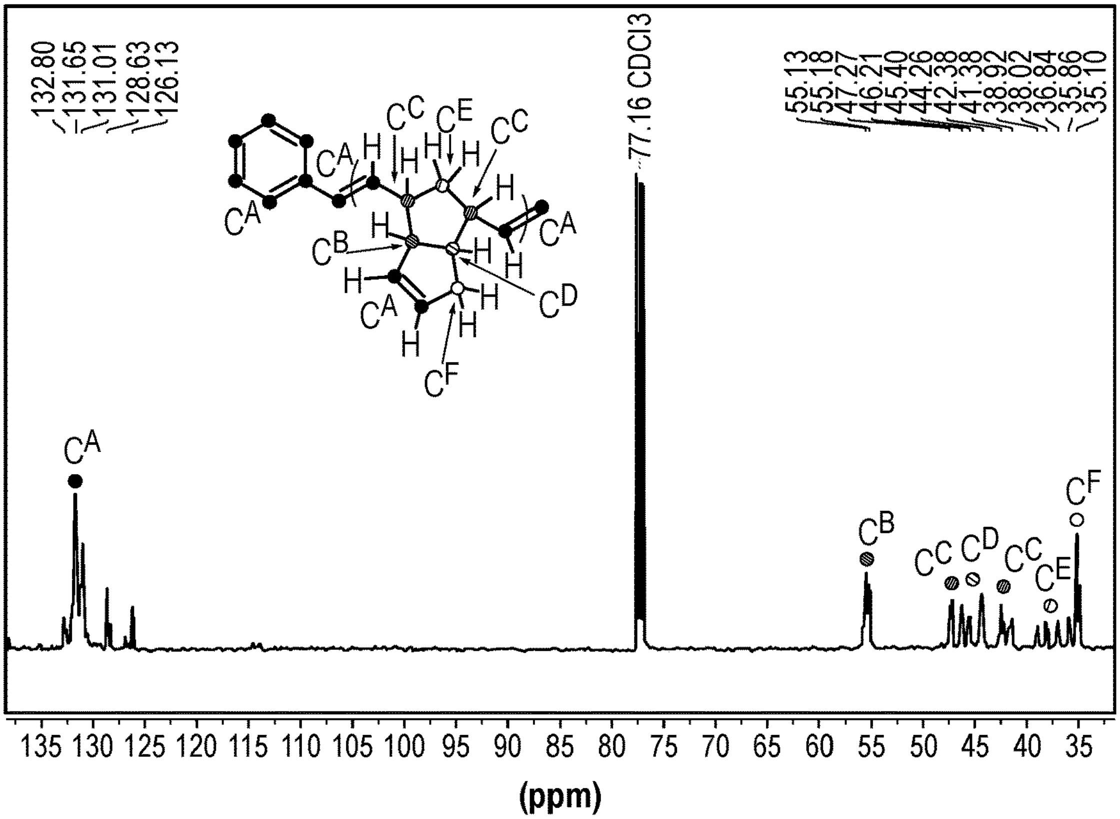
FIG. 8 illustrates a $^{13}C\{^{1}H\}$ NMR spectrum in chloroform-d of o(DCPD) prepared with a 10:1 molar ratio of DCPD to styrene, the o(DCPD) not exhibiting chain opening as determined from a 1:1 integration of the bridge C resonances (55.4 ppm) to the methylidene resonances (39.0-35.8 ppm)

In another example, dicyclopentadiene (DCPD, 10 g, 76 mmol, 1 equiv.), styrene (0.88 mL, 7.6 mmol, 0.1 equiv.), $P(O^nBu)_3$ (1.4 μL, 5.1 μmol, 70 ppm), and G2 (4.3 mg, 5.1 μmol, 70 ppm) were used to prepare a resin for frontal oligomerization. Solid DCPD was liquefied with styrene (0.44 mL), and subsequently a solution of G2 and $P(O^nBu)_3$ in styrene (0.44 mL) was added to the monomer solution to afford the oligomerization resin. Other phosphite esters of formula $P(OR^3)_3$ may be added, where all of the $R^3$ groups are simultaneously or each independently $(C_1-C_{20})$alkyl, such as methyl, ethyl, n-butyl, or tert-butyl, or aryl, such as phenyl. The resin was added to a 25×150 mm glass test tube, and FROMO was initiated with a hot soldering iron (300-400° C.) at the liquid-to-air interface. Upon initiation, a hot reaction front formed and traversed down the test tube with a monomer-to-oligomer interface. Full monomer consumption occurred within 30 seconds. The temperatures achieved during this frontal oligomerization process were sufficient to liquefy the resultant material; upon cooling, the oligomer solidified into a glass-like, brittle material. The oligomer was dissolved in chloroform (50 mL), and was then precipitated form solution with the addition of methanol (100 mL) to afford a stick white solid. The solid was washed twice with additional methanol (100 mL) to provide o(DCPD) as a white solid. Volatile components were removed under reduced pressure inside a vacuum oven set to 50° C. This material was crushed into a fine white powder (9.8 g, 91% mass recovery). The material is soluble in chlorinated solvents, ENB, and DCPD. By $^1$H NMR spectroscopy, the species exists as an oligomer of $\chi_n \approx 12$ ($M_w \approx 1.9$ kDa) by end group analysis of the CHPh resonances. By MALDI-MS, the species exists as a distribution of short-chain oligomers, ranging from $3 \leq \chi_n \leq 40$; the $M_n$ of oligomers as a function of styrene is illustrated in FIG. 6 and Table 2 below. A $^1$H NMR spectrum of the oligomer produced from the formulation including a 10:1 molar ratio of DCPD to styrene is illustrated in FIG. 7 and a $^{13}$C NMR spectrum is illustrated in FIG. 8.

Table 2 illustrates that number-average degree of polymerization and median degree of polymerization depend on the molar ratio of DCPD to styrene.

TABLE 2

| DCPD/styrene molar ratio | Average $X_n$ (End Group) | Median $M_n$ (MALDI) | Average $X_n$ (MALDI) | Mass (% Yield) |
|---|---|---|---|---|
| 5:1 | 4.8 | 578 | 3.6 | 27.8 g (80) |
| 10:1 | 11.6 | 1865 | 13.3 | 27.7 g (86) |
| 20:1 | 18.5 | 1974 | 14.9 | 27.1 g (87) |
| 35:1 | 27.8 | 2299 | 16.6 | 29.7 (97) |

Figure 9:
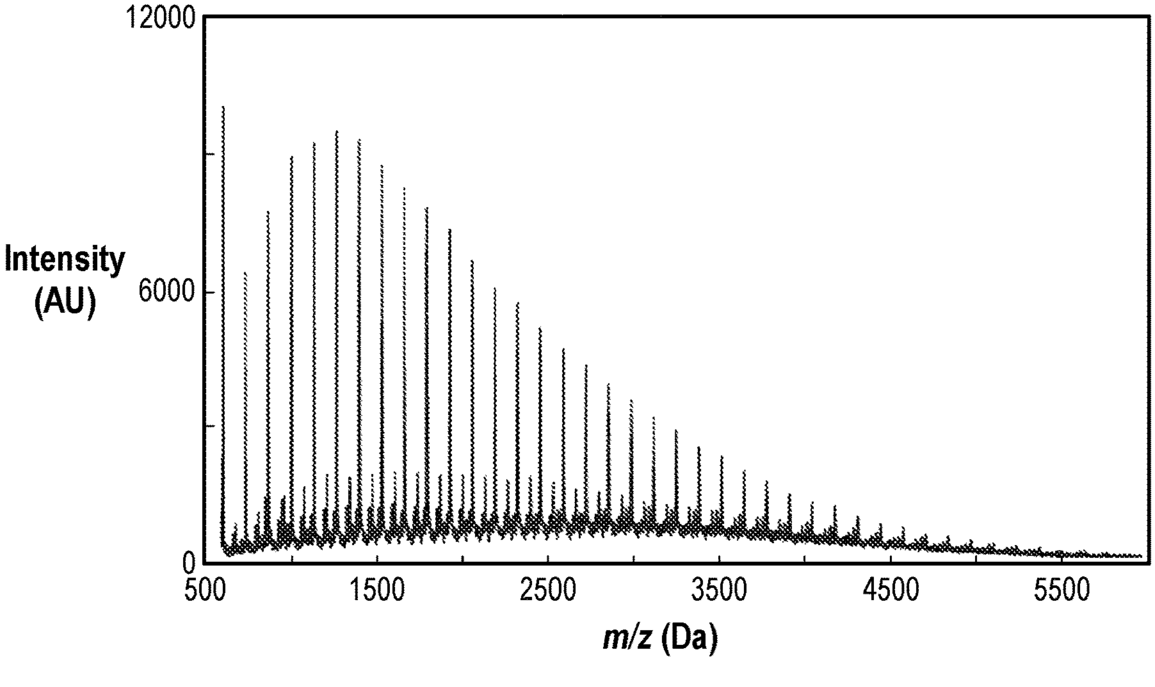
FIG. 9 illustrates a MALDI mass spectrum of o(DCPD) prepared with a 10:1 molar ratio of DCPD to styrene.

As illustrated in FIG. 9, the dominant oligomeric species range from a chain length of 3 to 40. The distribution is centered at n=10 and 11, with a y, of 13.3. The masses correspond to oligomers terminated with $=CH_2/=CHPh$ on either end of the structure and fly as the $Ag^+$ adducts. The smaller repeating series located between the dominant series are analogous oligomers terminated with either $=CH_2/=CH_2$ or $=CHPh/=CHPh$ on either end as the $Ag^+$ adduct.

MS (MALDI) m/z calc'd for $[M_n$+CHPh+Ag]+: 871.3 ($\chi_n$=6), 1137.5 ($\chi_n$=7), 1267.4 ($\chi_n$=8), 1399.7 ($\chi_n$=9), 1531.7 ($\chi_n$=10), 1663.8 ($\chi_n$=11), 1795.5 ($\chi_n$=12), 1928.0 ($\chi_n$=13), 2060.0 ($\chi_n$=14).

B. General Synthesis of o(ENB)

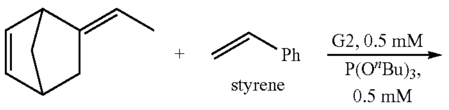

ENB

-continued

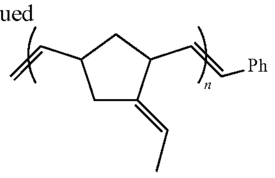

o(ENB)

Figure 10A:
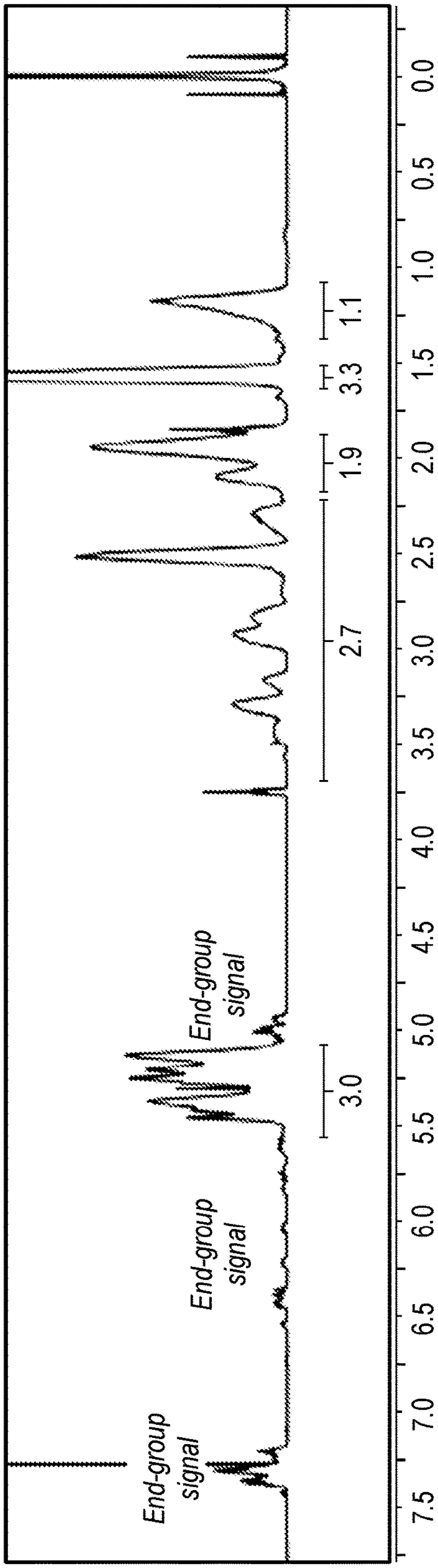
FIG. 10A illustrates a $^{1}$H NMR spectrum (499.7 MHz, chloroform-d with 1% v/v $SiMe_4$) of o(ENB) derived from Formulation 7.
Figure 10B:
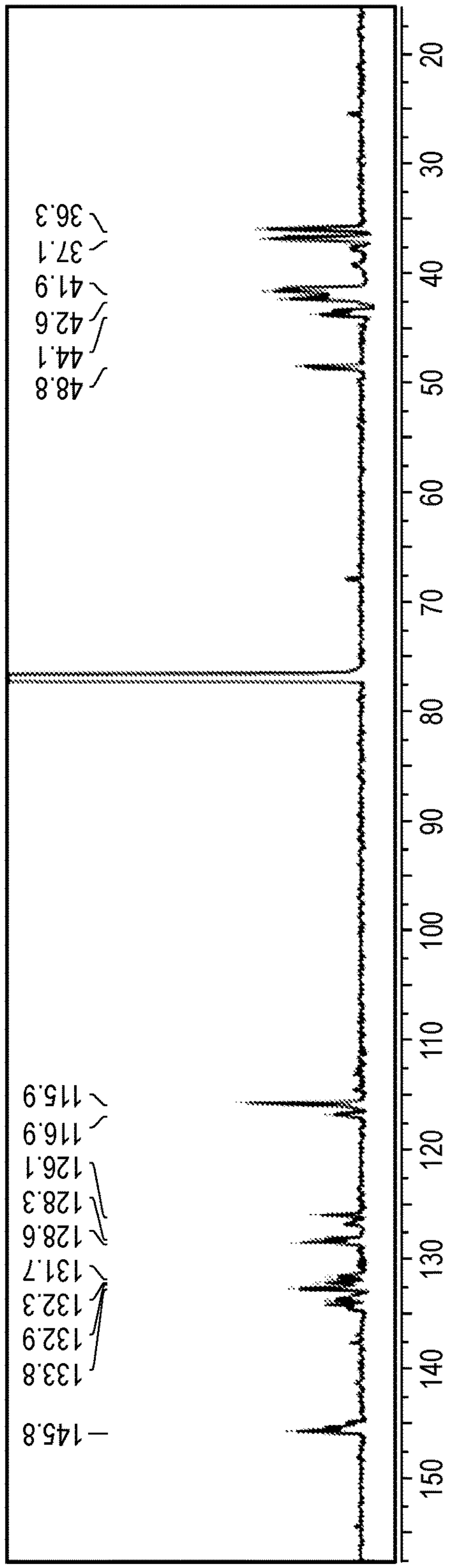
FIG. 10B illustrates a $^{13}C\{^{1}H\}$ spectrum (126 MHz, chloroform-d with 1% v/v $SiMe_4$) of o(DCPD) derived from Formulation 7.
Figure 11A:
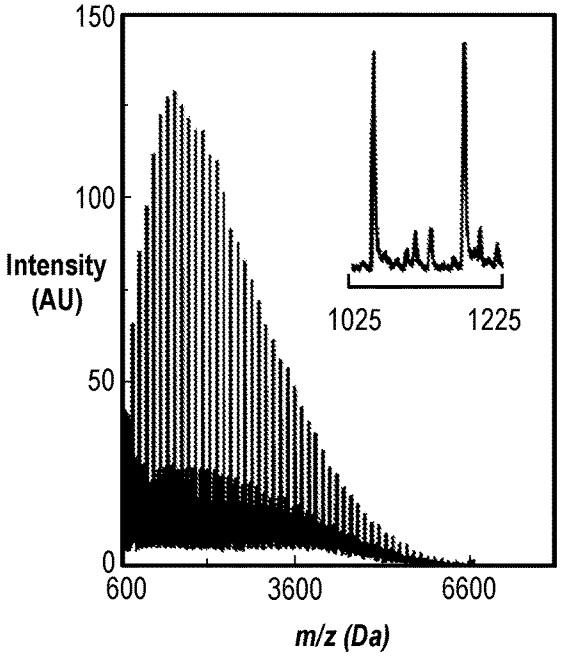
FIG. 11A illustrates a MALDI-TOF mass spectrum of o(ENB) terminated with styrene at a 5:1 molar ratio of ENB to styrene (Formulation 7)
Figure 11B:
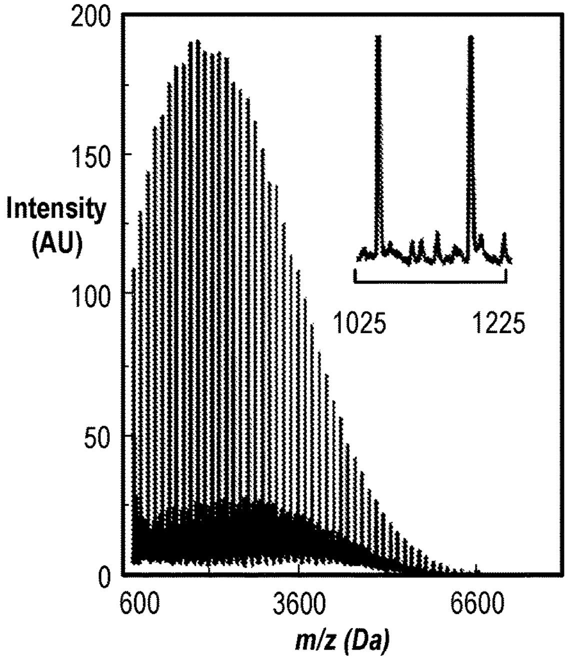
FIG. 11B illustrates a MALDI-TOF mass spectrum of o(ENB) terminated with styrene at a 10:1 molar ratio of ENB to styrene (Formulation 8)
Figure 11C:
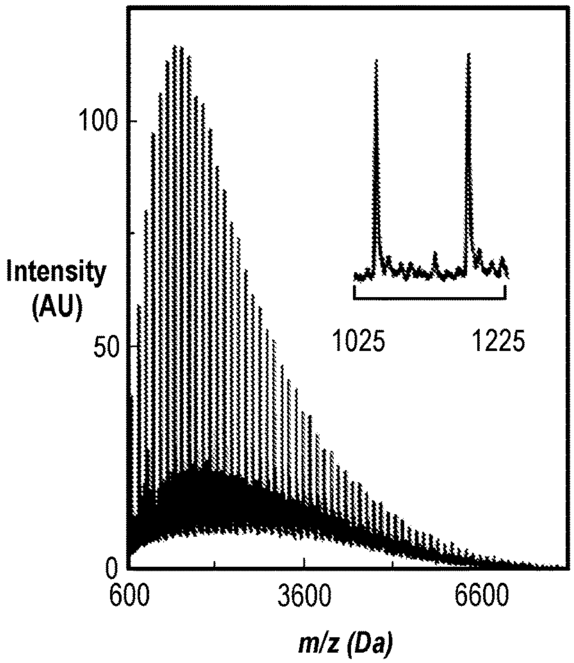
FIG. 11C illustrates a MALDI-TOF mass spectrum of o(ENB) terminated with styrene at a 20:1 molar ratio of ENB to styrene (Formulation 9)
Figure 11D:
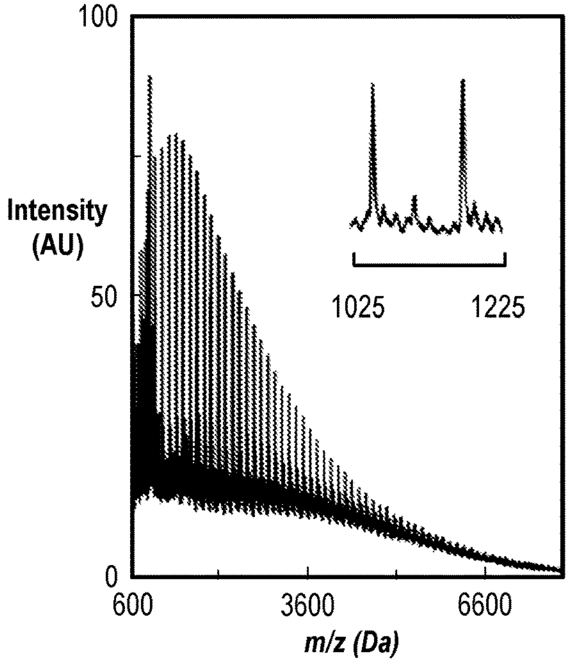
FIG. 11D illustrates a MALDI-TOF mass spectrum of o(ENB) terminated with styrene at a 35:1 molar ratio of ENB to styrene (Formulation 10)
Figure 12:
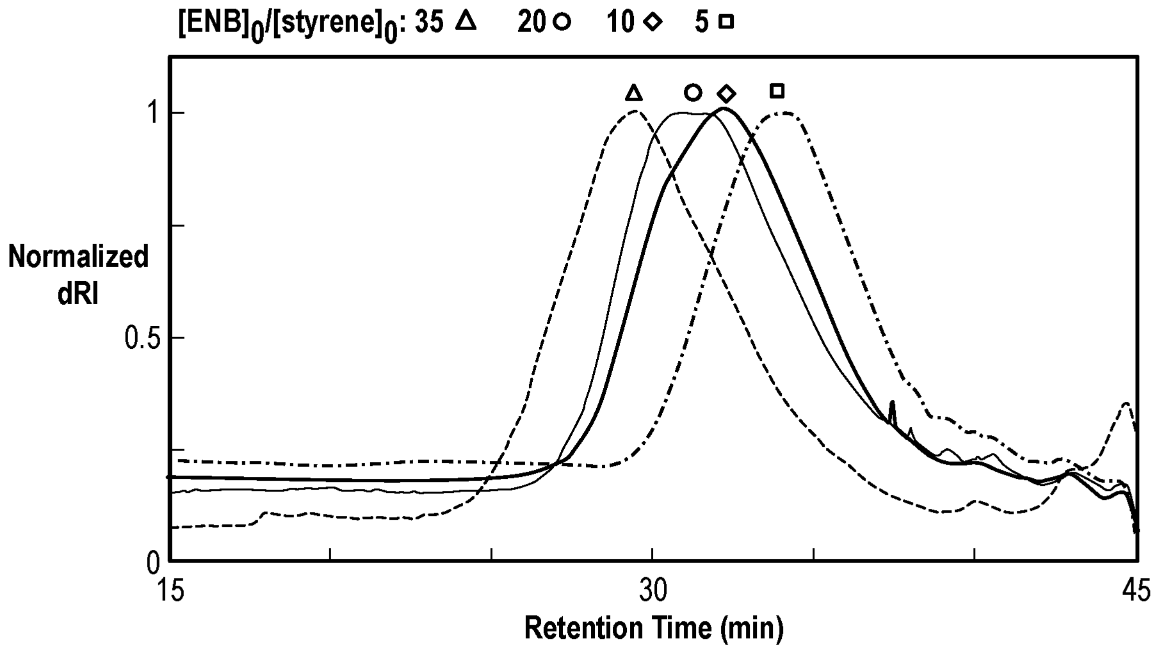
FIG. 12 illustrates size exclusion chromatography traces for o(ENB) with various molar ratios of ENB to styrene (Formulations 7-10)

Solvent-free resins employed for frontal oligomerization were prepared with the following exemplary procedure for formulation composition 7. Specific formulation compositions, including formulation composition 7, are found in Table 3 below. For formulation 7: ENB (5.2 mL, 38 mmol, 5 equiv.), styrene (0.9 mL, 7.6 mmol, 1 equiv.), P(O$^n$Bu)$_3$ (0.7 μL, 2.5 μmol, 0.5 mM), and G2 (2.0 mg, 2.5 μmol, 0.5 mM). A solution of G2 and P(O$^n$Bu)$_3$ in styrene (0.9 mL) was added to the monomer solution to afford the oligomerization resin. The resin was added to a 13×100 glass test tube, and frontal ring-opening metathesis oligomerization (FROMO) was initiated by touching a hot soldering iron to the glass at the liquid-to-air interface. The oligomer produced by the FROMO reaction was dissolved in dichloromethane (50 mL) and was then precipitated from solution with the addition of methanol (300 mL) to afford a sticky white solid. The solid was washed twice with additional methanol (200 mL) to provide oligo-ethylidene norbornene (o(ENB)) as a white solid. Volatile components were removed under reduced pressure over 16 h. The material was crushed into a fine white powder (2.26 g, 42% mass recovery). Full NMR spectra are illustrated in FIGS. 10A and 10B. Representative MALDI-TOF traces are illustrated in FIGS. 11A-11D. Representative SEC traces are illustrated in FIG. 12. Tabulated molecular weight data from end-group analysis, MALDI, and SEC are provided in Table 8.

TABLE 3

Composition of resin solutions with various ENB-to-styrene molar ratios at fixed amounts of G2 (2.0 mg, 2.5 μmol) and P(O$^n$Bu)$_3$ (0.7 μL, 2.5 μmol)

| Formulation Number | ENB/styrene mol/mol ratio | ENB (mL) | Styrene (mL) | Mass Recovery (g) | Mass Yield (%) |
|---|---|---|---|---|---|
| 7 | 5:1 | 5.2 | 0.9 | 2.26 | 42 |
| 8 | 10 | 5.2 | 0.4 | 2.27 | 46 |
| 9 | 20 | 5.2 | 0.2 | 4.16 | 87 |
| 10 | 35 | 5.2 | 0.1 | 4.61 | >95 |

C. General Synthesis of o(NBE)

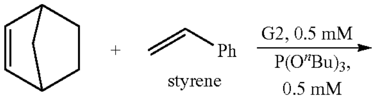

NBE

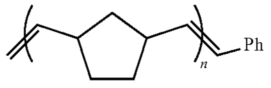

o(NBE)

Figure 13A:
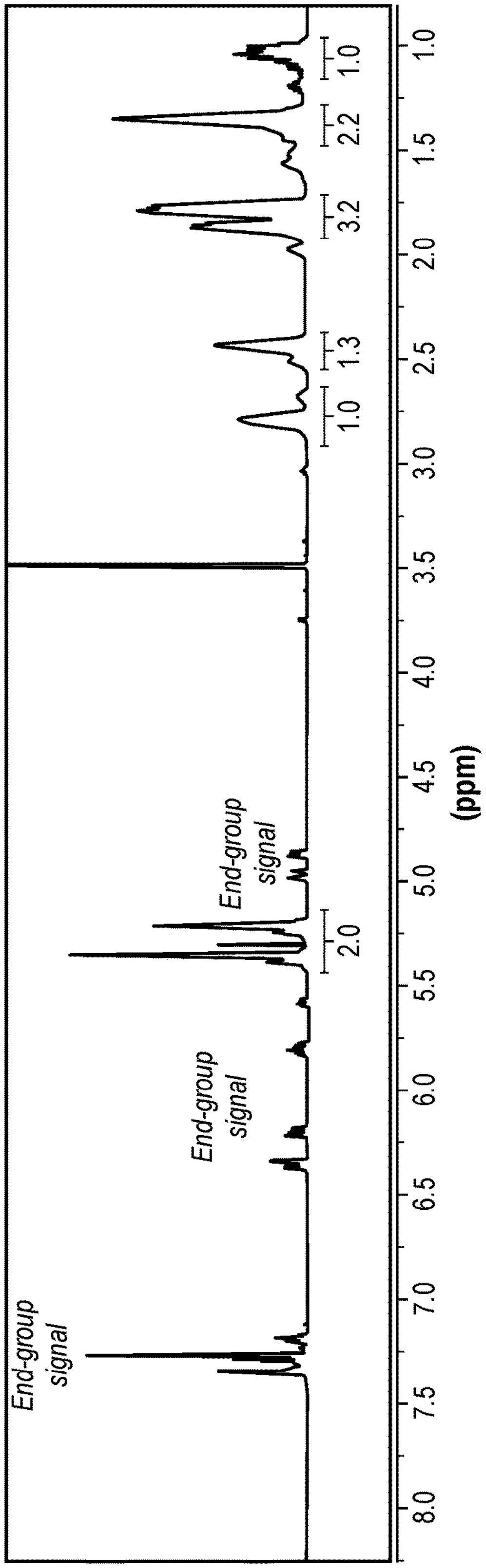
FIG. 13A illustrates a $^{1}$H NMR spectrum (499.7 MHz, chloroform-d with 1% v/v $SiMe_4$) of o(NBE) derived from Formulation 11.
Figure 13B:
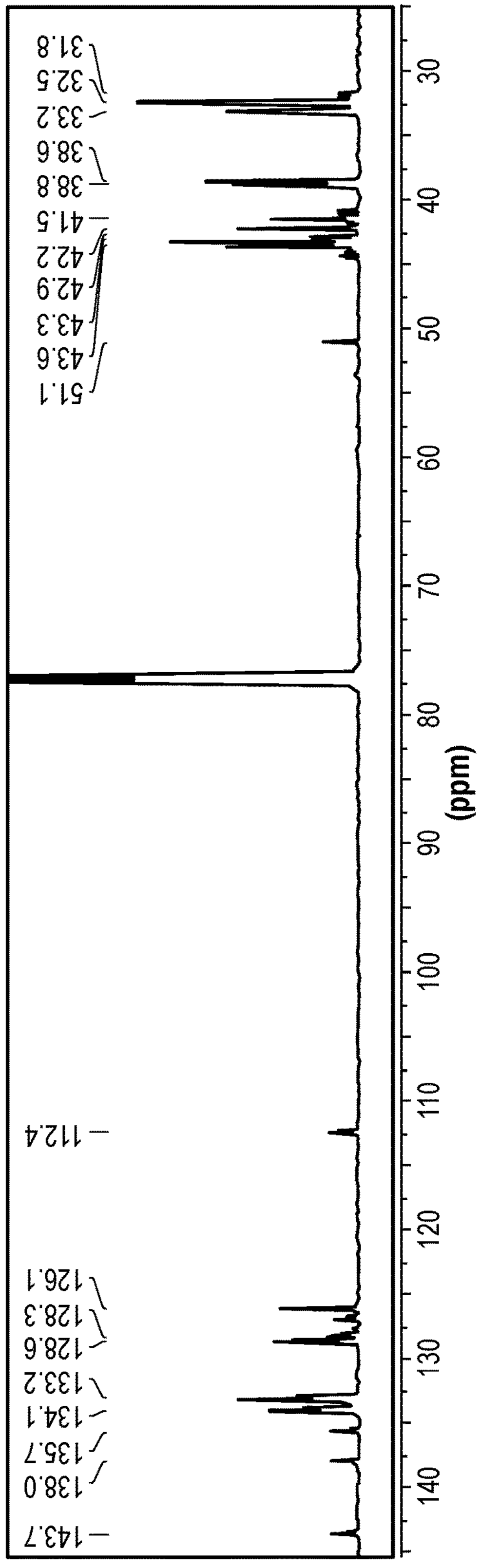
FIG. 13B illustrates a $^{13}$C NMR spectrum (126 MHz, chloroform-d with 1% v/v $SiMe_4$) of o(NBE) derived from Formulation 11.
Figure 14A:
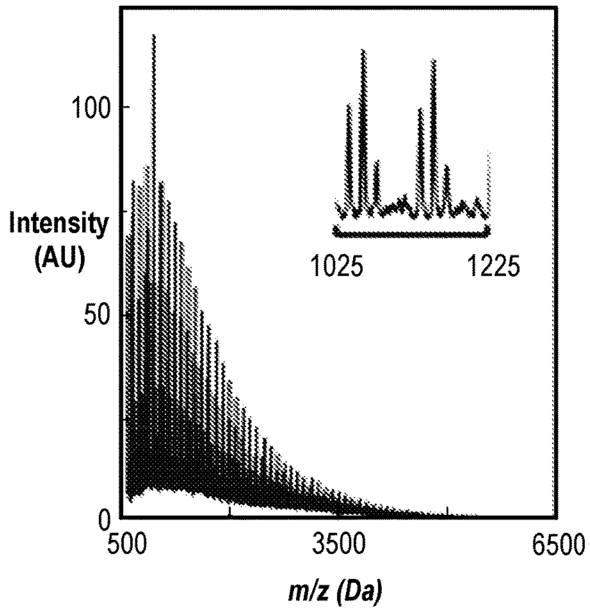
FIG. 14A illustrates a MALDI-TOF mass spectrum of o(NBE) terminated with styrene at a 5:1 molar ratio of NBE to styrene (Formulation 11)
Figure 14B:
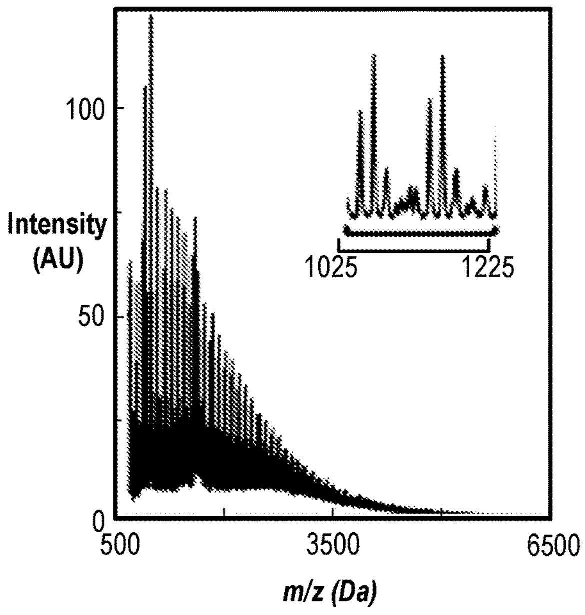
FIG. 14B illustrates a MALDI-TOF mass spectrum of o(NBE) terminated with styrene at a 10:1 molar ratio of NBE to styrene (Formulation 12)
Figure 15:
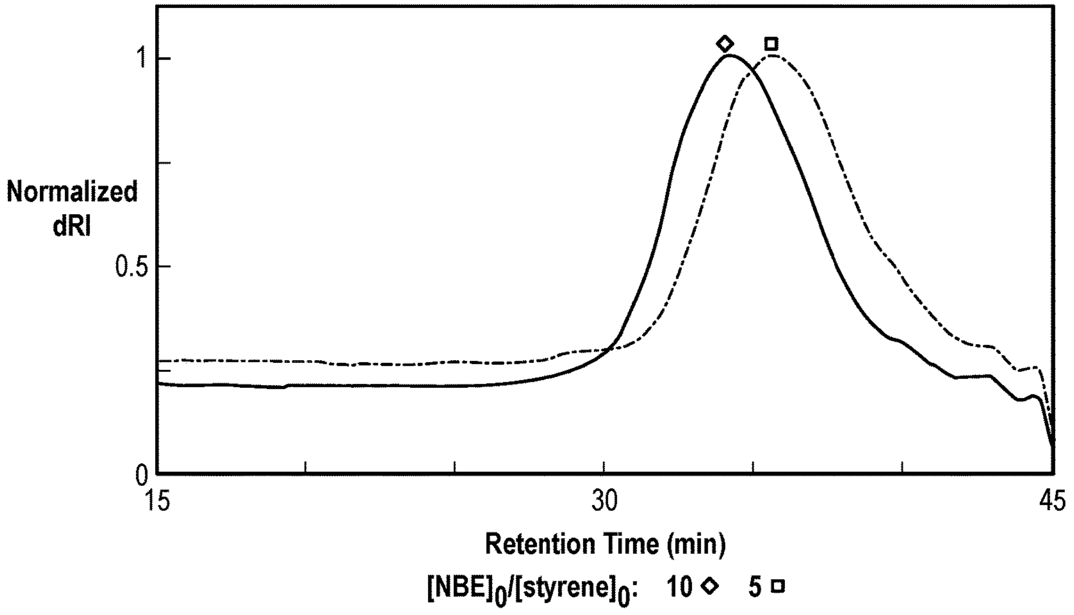
FIG. 15 illustrates size exclusion chromatography traces for o(NBE) with various molar ratios of NBE to styrene (Formulations 11-12)

Solvent-free resins employed for frontal oligomerization were prepared with the following exemplary procedure for formulation composition 11. Specific formulation compositions, including formulation composition 11, are found in Table 4 below. For formulation 11: NBE (5.2 g, 55 mmol, 5 equiv.), styrene (1.3 mL, 11 mmol, 1 equiv.), $P(O^nBu)_3$ (0.7 μL, 2.5 μmol, 0.5 mM), and G2 (2.0 mg, 2.5 μmol, 0.5 mM). A solution of G2 and $P(O^nBu)_3$ in styrene (0.2 mL) was added to a solution of NBE (5.2 mg) in styrene (1.1 mL) to afford the oligomerization resin. The resin was added to a 13×100 mm glass test tube, and frontal ring-opening metathesis oligomerization (FROMO) was initiated by touching a hot soldering iron to the glass at the liquid-to-air interface. The oligomer produced by the FROMO reaction was dissolved in dichloromethane (50 mL) and was then precipitated from solution with the addition of methanol (200 mL) to afford a sticky white solid. The solid was washed twice with additional methanol (200 mL) to provide oligo-norbornene (o(NBE)) as a white solid. Volatile components were removed under reduced pressure over 16 h. The material was crushed into a fine white powder (3.76 g, 59% mass recovery). Full NMR spectra are provided in FIGS. 13A-13B. Representative MALDI-TOF traces are illustrated in FIGS. 14A-14B. Representative SEC traces are illustrated in FIG. 15. Tabulated molecular weight data from end-group analysis, MALDI, and SEC are provided in Table 8.

TABLE 4

Composition of resin solutions with various NBE-to-styrene molar ratios at fixed amounts of G2 (2.0 mg, 2.5 μmol) and $P(O^nBu)_3$ (0.7 μL, 2.5 μmol)

| Formulation Number | NBE/styrene mol/mol ratio | NBE (g) | Styrene (mL) | Mass Recovery (g) | Mass Yield (%) |
|---|---|---|---|---|---|
| 11 | 5 | 5.2 | 1.3 | 3.76 | 59 |
| 12 | 10 | 5.2 | 0.6 | 3.87 | 67 |

D. Synthesis of o(DCPD) with 3-Bromostyrene or Ethyl Vinyl Ether (EVE) as Chain Transfer Agent

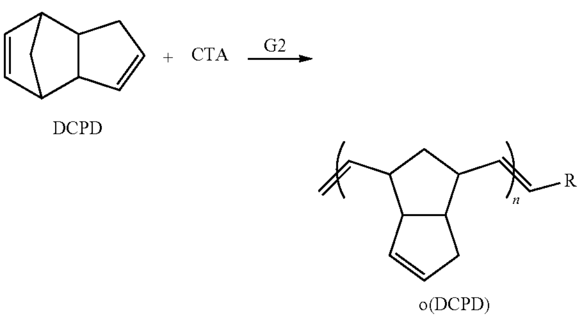

DCPD
o(DCPD)

Figure 16A:
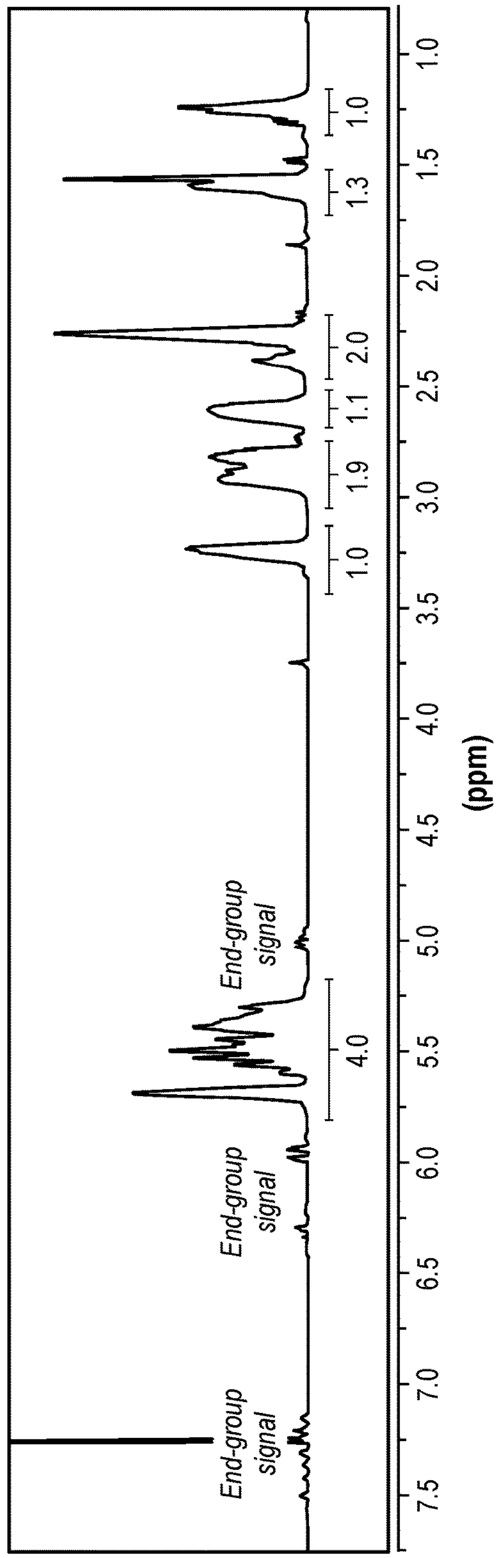
FIG. 16A illustrates a $^{1}$H NMR spectrum (499.7 MHz, chloroform-d with 1% v/v $SiMe_4$) of o(DCPD) derived from Formulation 13.
Figure 16B:
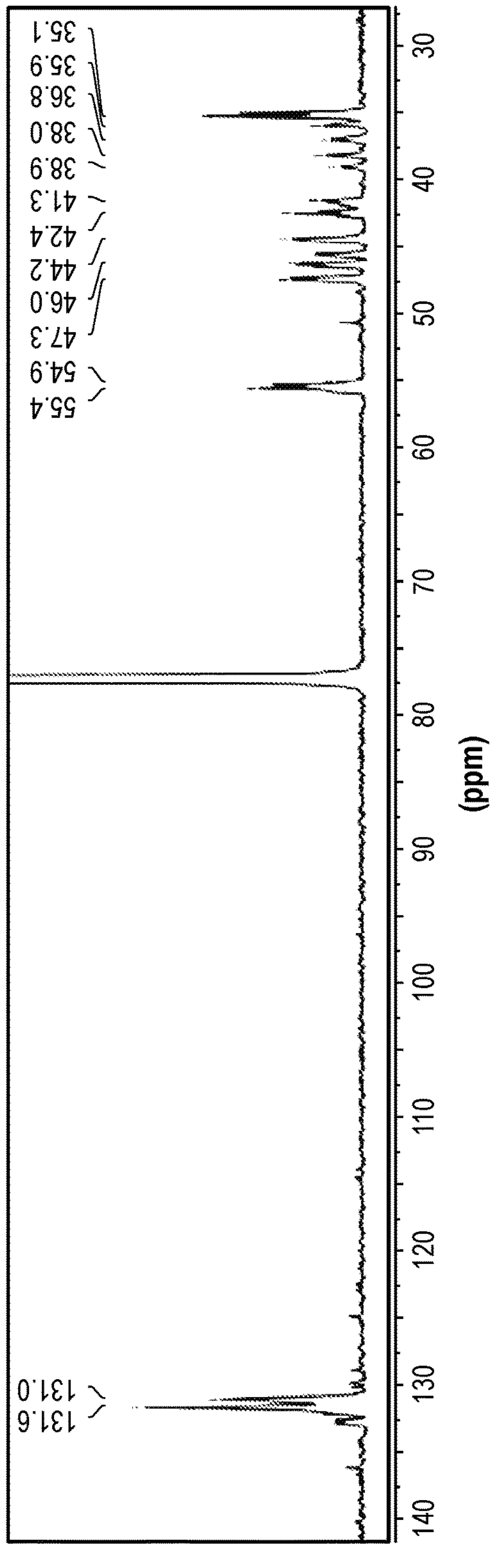
FIG. 16B illustrates a $^{13}C\{^{1}H\}$ NMR spectrum (126 MHz, chloroform-d with 1% v/v $SiMe_4$) of o(DCPD) derived from Formulation 13.
Figure 17A:
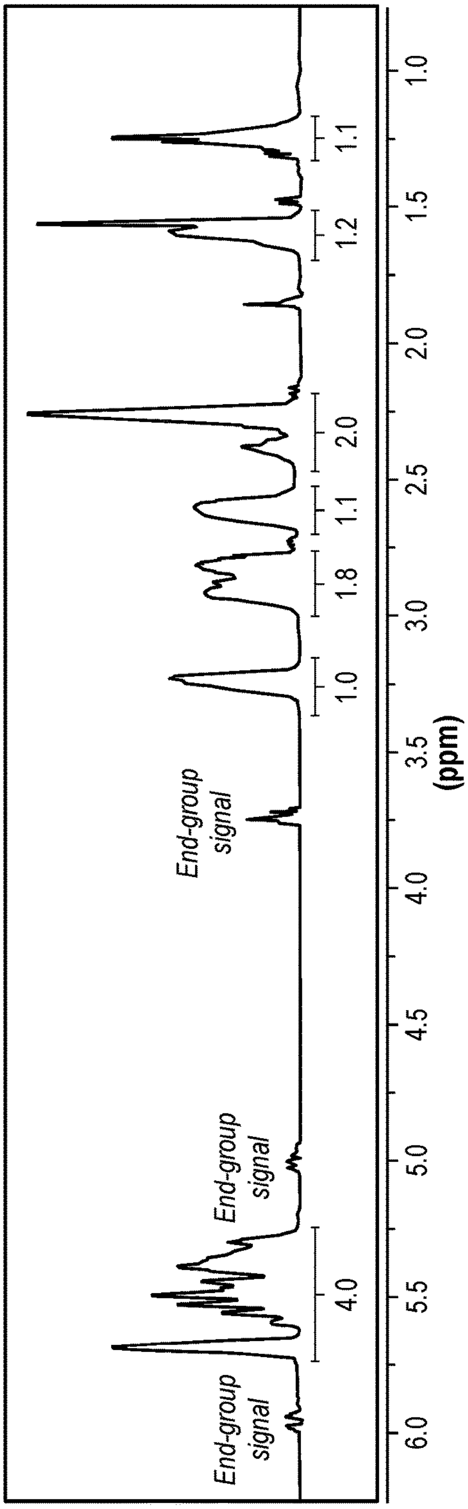
FIG. 17A illustrates a $^{1}$H NMR spectrum (499.7 MHz, chloroform-d with 1% v/v $SiMe_4$) of o(DCPD) derived from Formulation 14.
Figure 17B:
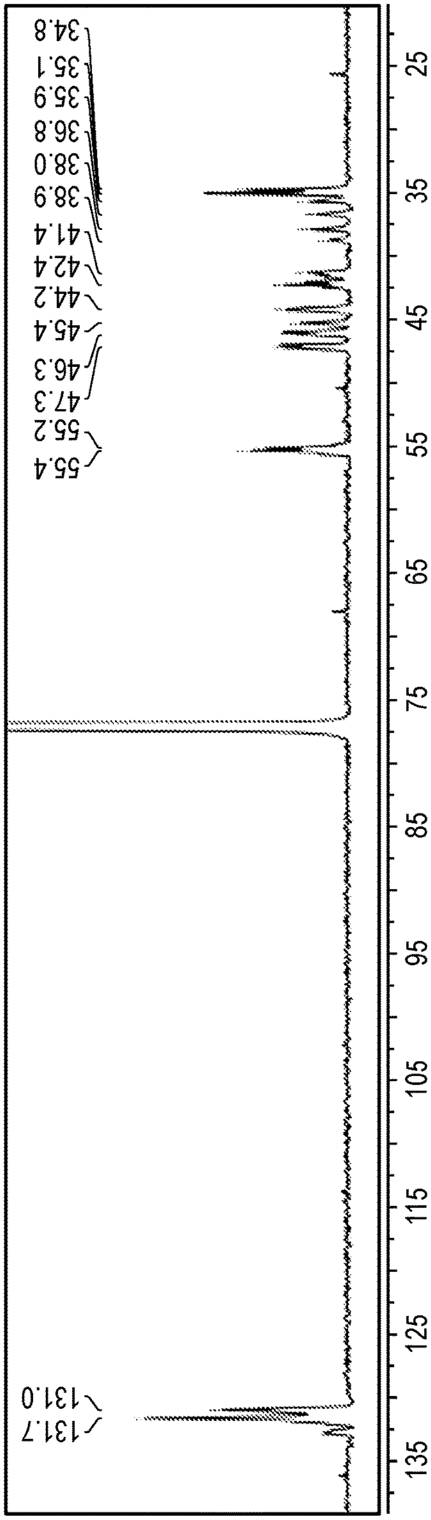
FIG. 17B illustrates a $^{13}C\{^{1}H\}$ NMR spectrum (126 MHz, chloroform-d with 1% v/v $SiMe_4$) of o(DCPD) derived from Formulation 14.
Figure 18A:
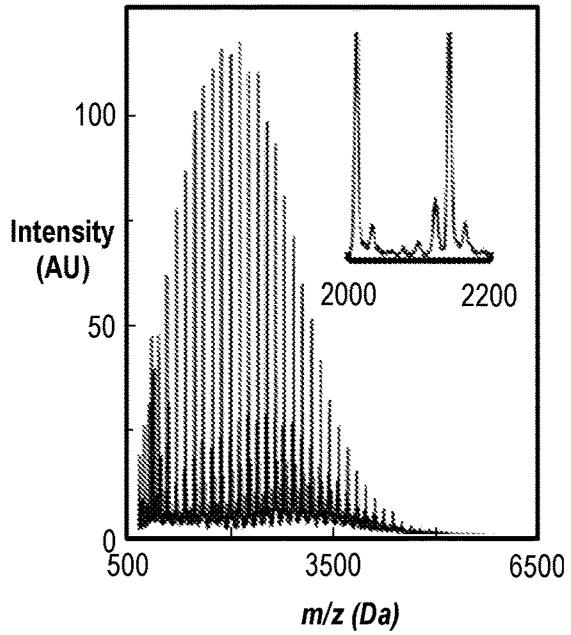
FIG. 18A illustrates a MALDI-TOF mass spectrum of o(DCPD) terminated with 3-bromostyrene (Formulation 13)
Figure 18B:
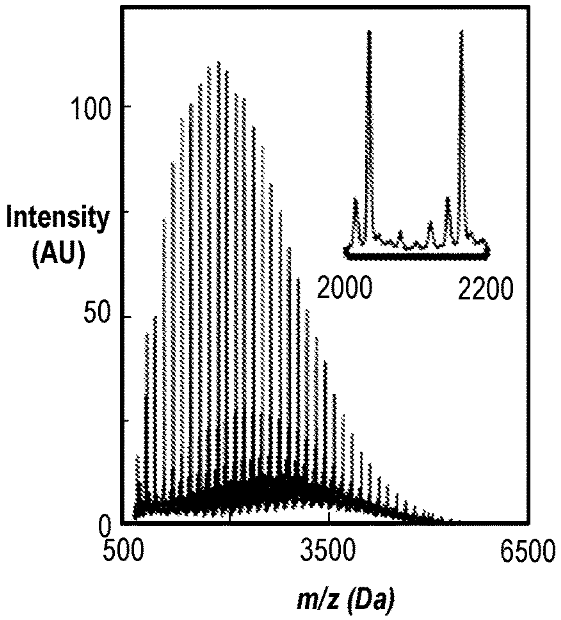
FIG. 18B illustrates a MALDI-TOF mass spectrum of o(DCPD) terminated with EVE (Formulation 14)
Figure 19:
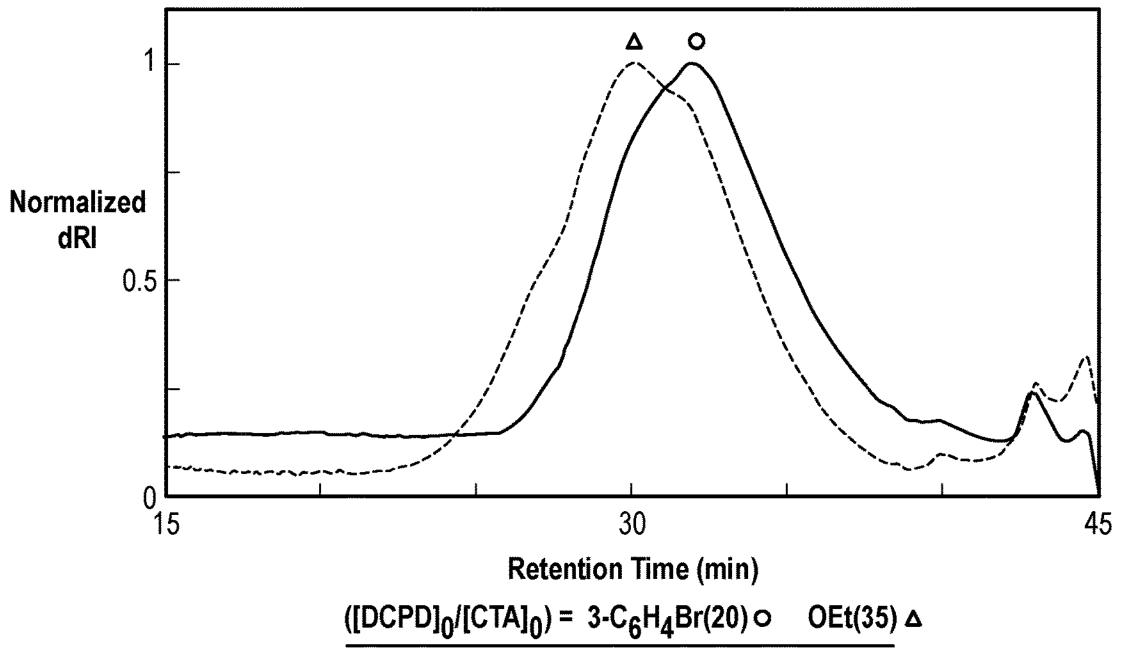
FIG. 19 illustrates size exclusion chromatography traces for o(DCPD) for o(DCPD) with 3-bromostyrene (Formulation 13) and EVE (Formulation 14)

The procedure for o(DCPD) synthesis described above was employed, but with either 3-bromostyrene or EVE as the chain transfer agent. Specific conditions are found below in Table 5. FROMO occurs at DCPD/EVE ratios greater than 30 and without $P(O^nBu)_3$ added. FROMO quenching may occur with higher EVE-content resins or in the presence of $P(O^nBu)_3$. Full NMR spectra are illustrated in FIGS. 16A and 16B for Formulation 13 (with 3-Bromostyrene) and FIGS. 17A and 17B for Formulation 14 (with EVE). Representative MALDI-TOF traces are illustrated in FIGS. 18A and 18B. Representative SEC traces are illustrated in FIG. 19. Tabulated molecular weight data from end-group analysis, MALDI, and SEC are provided in Table 8.

TABLE 5

Comparison of resin solutions with various DCPD-to-chain-transfer-agent molar ratios at fixed amounts of G2 (2.0 mg, 2.5 μmol) and $P(O^nBu)_3$ (0.7 μL, 2.5 μmol).

| Formulation Number | Chain Transfer Agent ("CTA") | DCPD/CTA | DCPD (g) | CTA (mL) | Mass Recovery (g) | Mass Yield (%) |
|---|---|---|---|---|---|---|
| 13 | 3-Bromostyrene | 20 | 5.2 | 0.3 | 3.82 | 69 |
| 14[a] | EVE | 35 | 5.2 | 0.1 | 3.24 | 61 |

[a] $P(O^nBu)_3$ was not included in the resin mixture.

EVE may be conventionally used in ROMP reactions to quench polymerization. Under FROMO conditions, however, the heat of the reaction in neat resin was sufficient to induce catalytic turnover from "quenched" catalysts. Cyclopentene ring-opening appeared to occur more frequently with EVE as the CTA than with styrene, as illustrated in FIG. 20B. In samples prepared from 3-bromostyrene or EVE, species terminated by $=CH_2/=CHPh$ occur, which is attributed to the first oligomer generated by G2. The benzylidene of the precatalyst may act as a chain-end for the first oligomer generated in FROMO.

E. Synthesis of o(DCPD)-Butenol and o(DCPD)-Butenyl-NB Ester

1. Synthesis of o(DCPD)-Butenol

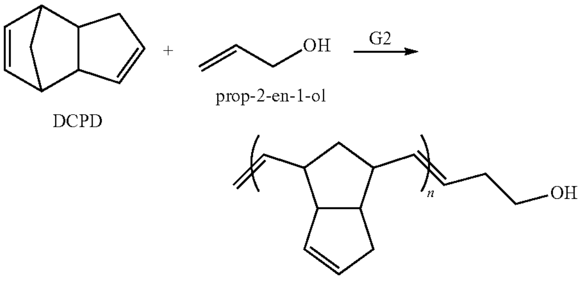

DCPD
prop-2-en-1-ol
o(DCPD)-butenol

Figure 21:
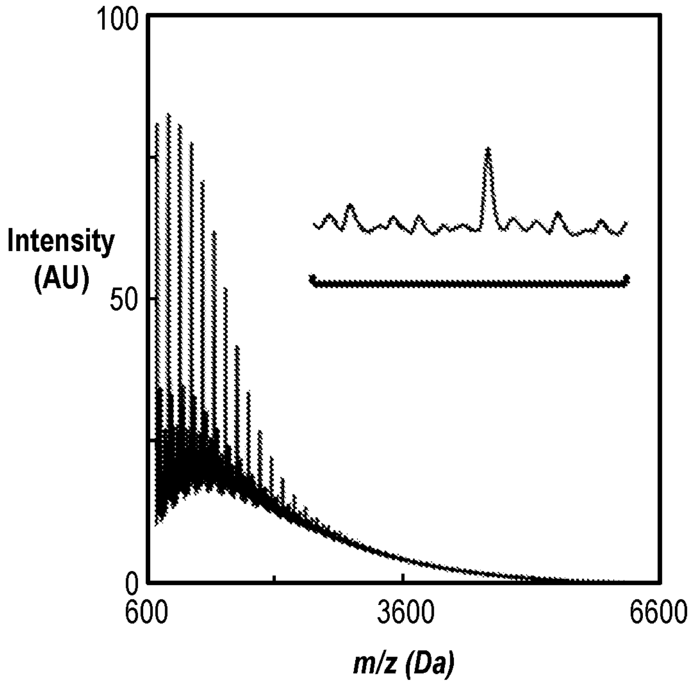
FIG. 21 illustrates a MALDI-TOF mass spectrum of o(DCPD)-butenol.
Figure 22:
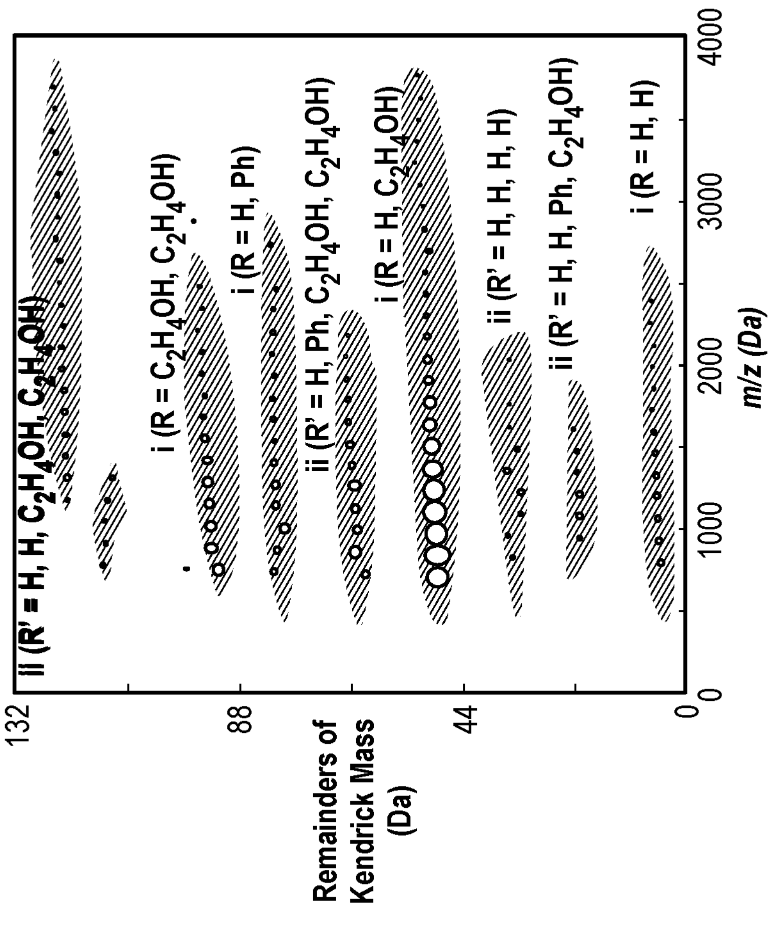
FIG. 22 illustrates Kendrick mass-analysis of o(DCPD)-butenol.
Figure 22:
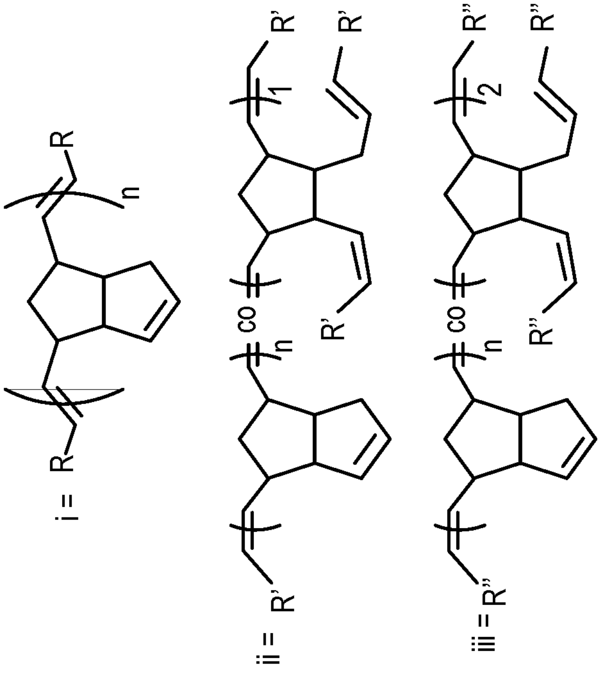

Solvent-free resins employed for frontal oligomerization were prepared with the following general composition: dicyclopentadiene (DCPD, 5 g, 38 mmol, 5 equiv.), prop-2-en-1-ol (1.0 mL, 11.6, 1 equiv.), and G2 (8 mg, 10 μmol, 2.0 mM). Solid DCPD was liquefied with prop-2-en-1-ol (0.5 mL), and subsequently a solution of G2 in prop-2-en-1-ol (0.5 mL) was added to the monomer solution to afford the oligomerization resin. The resin was added to a 25×150 mm glass test tube, and frontal ring-opening metathesis oligomerization (FROMO) was initiated with ah ot soldering iron at the liquid-to-air interface. Upon initiation, a hot reaction front formed and traversed down the test tube with a monomer-to-oligomer interface. Full monomer consumption occurred within 30 seconds. The temperatures achieved during the frontal oligomerization process were sufficient to liquefy the resultant material; upon cooling, the oligomer solidified into a glass-like, brittle material. The oligomer was dissolved in chloroform (50 mL), and was then precipitated from solution with the addition of methanol (100 mL) to afford a sticky white solid. The solid was washed twice with additional methanol (100 mL) to provide o(DCPD)-butenol as a white solid. Volatile components were removed under reduced pressure inside a vacuum oven set to 50° C. The material was crushed into a fine white powder (2.8 g, 48% mass recovery). The material is soluble in chlorinated solvents. The species exists as an oligomer of $X_n \approx 9$ ($M_w \approx 1.7$ kDa) by MALDI-MS as illustrated in FIG. 21. Kendrick analysis of the MALDI-MS, as illustrated in FIG. 22, indicated that the oligomers primarily exist as heterotelechic species with methylene and butenol chain ends. Moreover, the species exists as a distribution of short chain oligomers, ranging from $4 \leq X_n \leq 15$.

2. Synthesis of o(DCPD)-butenyl-NB Ester

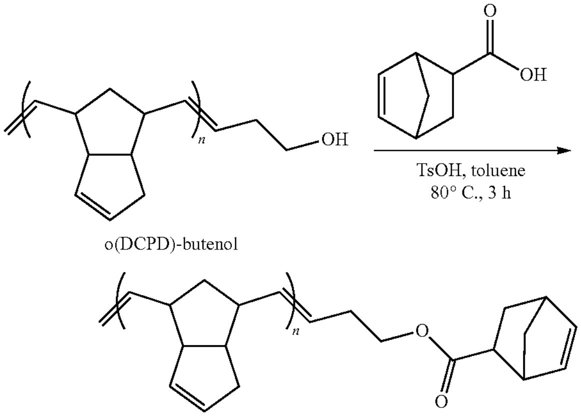

o(DCPD)-butenol o(DCPD)-butenyl-NB ester

Figure 23:
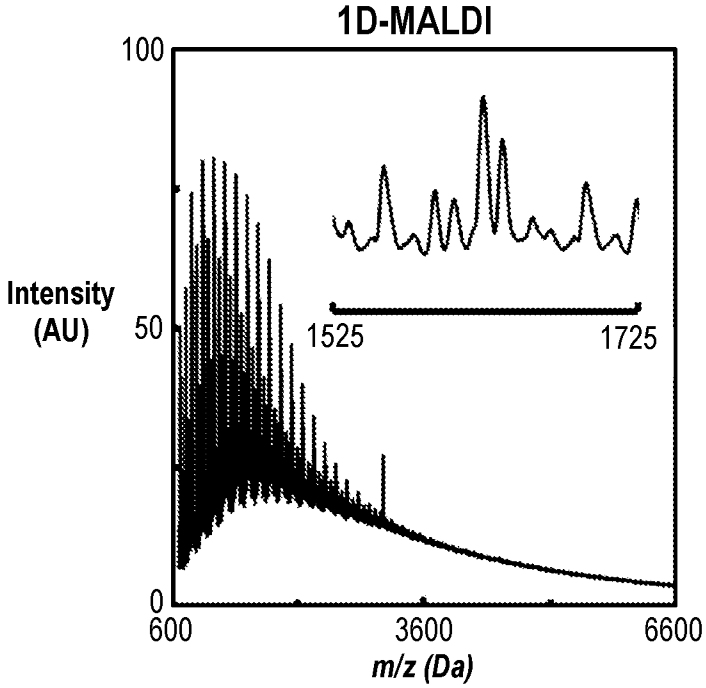
FIG. 23 illustrates a MALDI-TOF mass spectrum of o(DCPD)-butenyl-NB ester.
Figure 24:
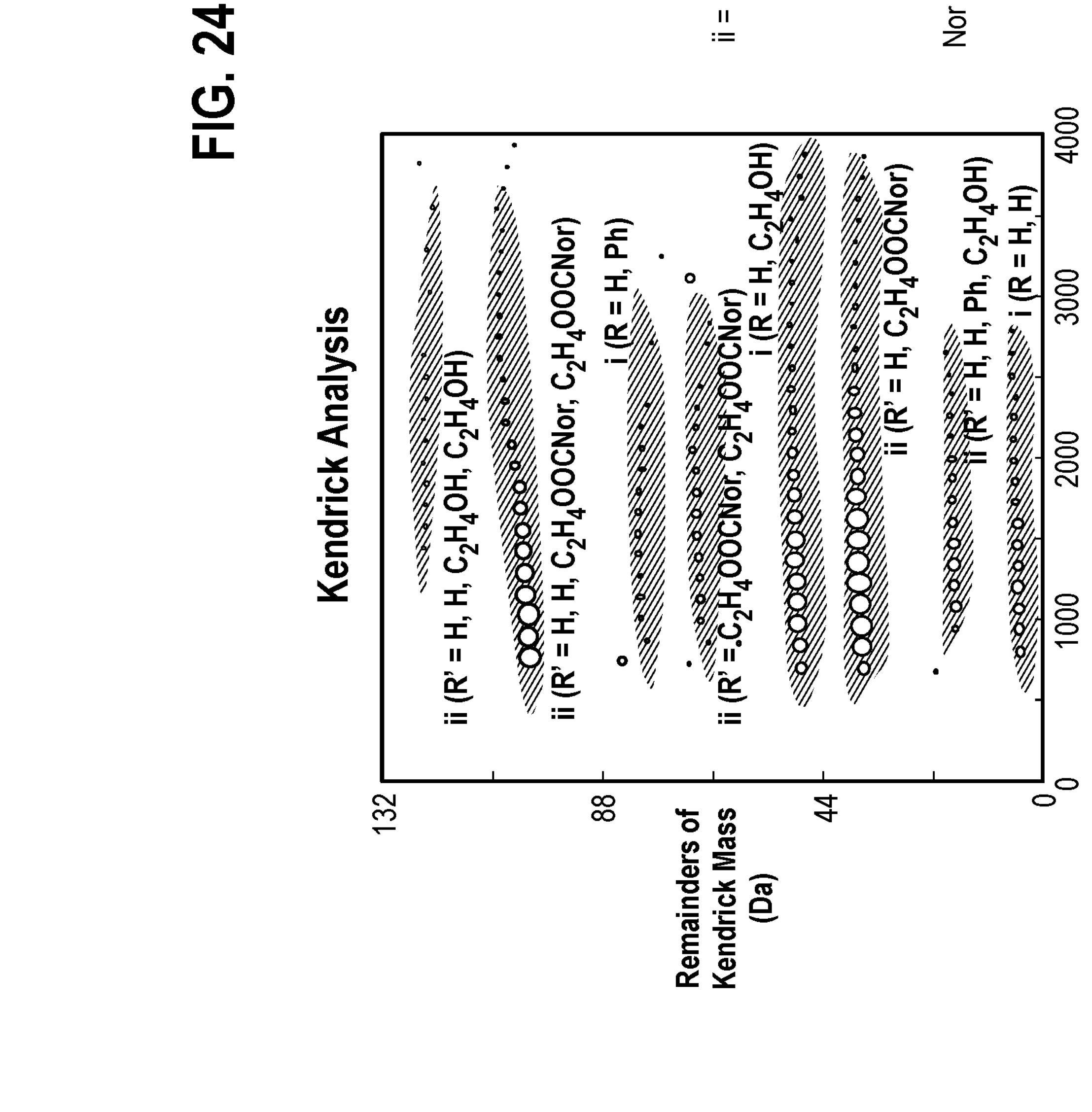
FIG. 24 illustrates Kendrick mass-analysis of o(DCPD)-butenyl-NB ester.
Figure 24:
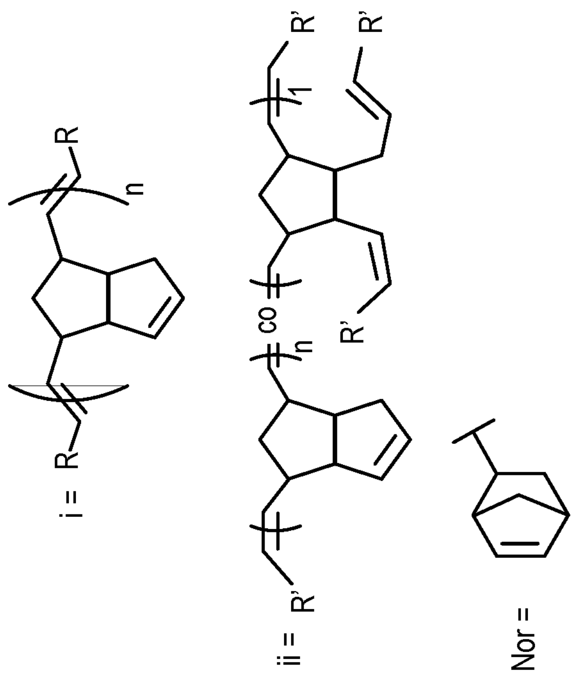

A sample of o(DCPD)-butenol (1 g, $M_w \approx 1.7$ kDa, 0.59 mmol, 1 equiv.) dissolved in toluene was treated with norbornene-2-carboxylic acid (160 mg, 1.19 mmol, 2 equiv.) and p-toluenesulfonic acid monohydrate (20 mg, 0.1 mmol, 20 mol %). The mixture was heated to 80° C. for 3 hours; over the course of heating, the reaction mixture darkened in color. After completion, the oligomeric products were precipitated from methanol (200 mL) and thoroughly washed (twice) with additional methanol after decanting (200 mL). Volatile components were removed under reduced pressure to afford the product as a black powder (0.8 g, 76%) soluble in most organic solvents. MALDI-MS (FIG. 23) and Kendrick analysis (FIG. 24) confirmed the presence of a norbornene-ester as the chain end.

F. Gel-State FROMP Reactions of oDCPD

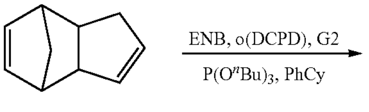

-continued

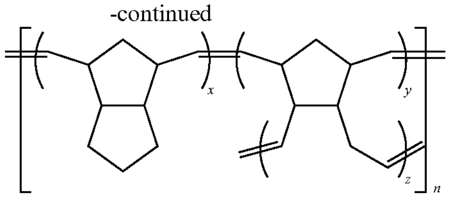

With oDCPD produced according to the processes described above in examples herein, the oligomers were submitted to rheological modifiers for gel-state FROMP reactions. Optimal resins may exhibit viscosities of at least 10 Pa·s. In the examples herein, the rheologically unmodified "base" resins may include a 95:5 mixture of DCPD:ENB. The use of a comonomer may depress the freezing point so as to liquefy the material. Rheological augmentation occurred after the addition of o(DCPD) to the base resin, which provided formulations of varying viscosities. Each resin also contained G2 (0.5 mM) and P(O$^n$Bu)$_3$ (0.5 mM) dissolved in minimal phenylcyclohexane ("PhCy"). The viscosities of the resins increased exponentially with the weight loading of added o(DCPD). Oligomers with larger $\overline{M}_n$ increased the viscosity to the greatest extent. Oligomers with longer chain lengths reduce molecular mobility within the resin matrix to a greater degree, which may result from internal friction between randomly coiled oligomer chains and surrounding monomers. Resins including oligomers (40 weight %) with a $\overline{M}_n$ of 2.7 kDa displayed viscosities suitable for extrusion (≈13 Pa·s).

Figure 25:
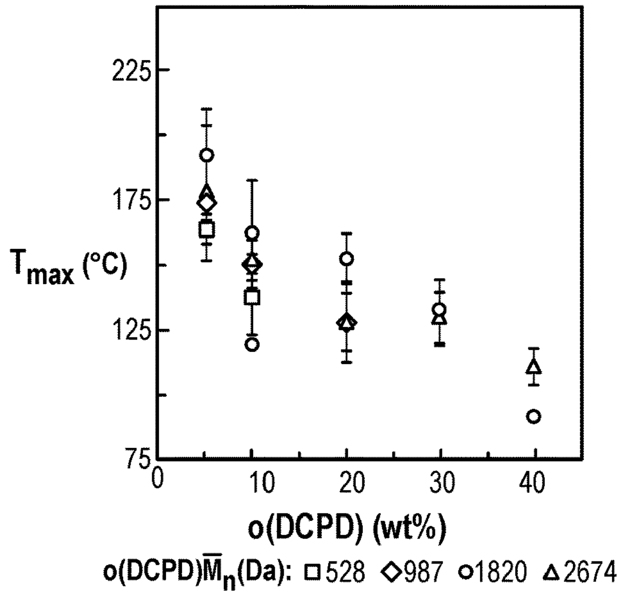
FIG. 25 illustrates maximum front temperature ($T_{max}$) as a function of o(DCPD) $\overline{M}_n$ and loading for FROMP resins including DCPD and ENB.
Figure 26:
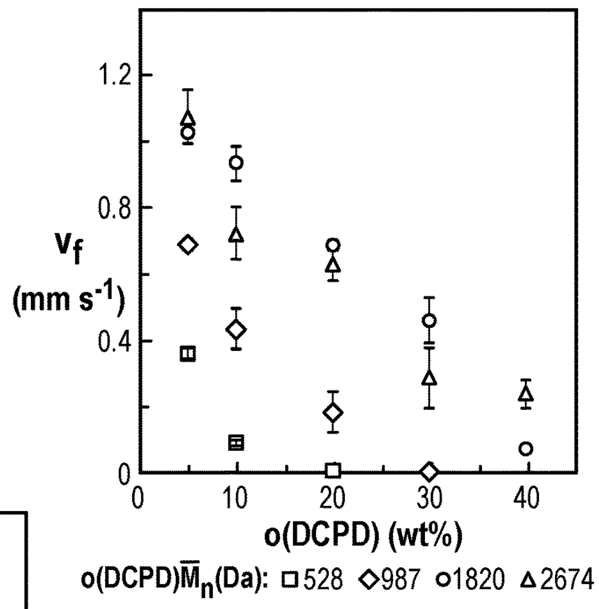
FIG. 26 illustrates front velocity ($v_f$) as a function of o(DCPD) $\overline{M}_n$ and loading for FROMP resins including DCPD and ENB.
Figure 27:
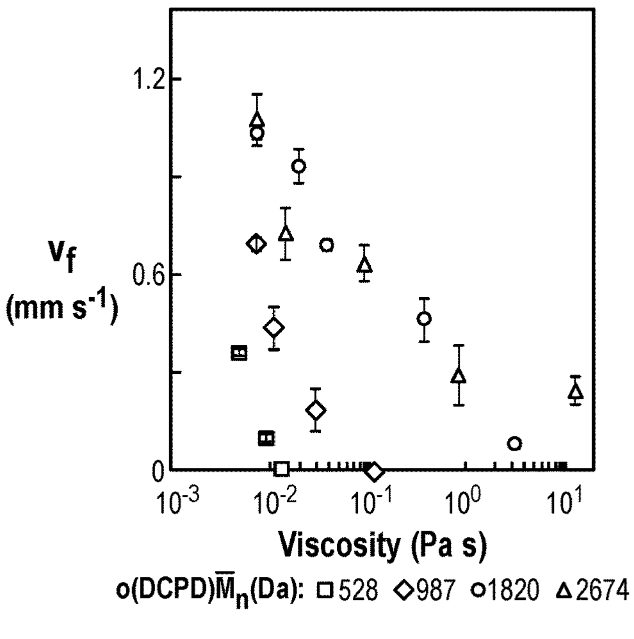
FIG. 27 illustrates a correlation plot of front velocity with resin viscosity for FROMP resins including DCPD and ENB.

The metrics associated with FROMP of these rheologically modified resins after thermal initiation were also analyzed. The steady-state front velocity ($v_f$) and maximum temperature achieved during FROMP ($T_{max}$) characterized the reaction process. Generally, $T_m$ax decreases with o(DCPD) content, regardless of the average oligomer chain length, as illustrated in FIG. 25. The reduction in the embodied energy of o(DCPD) versus DCPD may result in a depression in $T_{max}$. While the cyclopentene functionality may participate in FROMP, the oligomers do not substantially add to the reaction exothermicity and instead reduce the energy density of the resin. The observed $v_f$ also apparently diminishes with o(DCPD) content, as illustrated in FIG. 26. In contrast to $T_{max}$, the oligomer $\overline{M}_n$ may influence the $v_f$. Short-chain oligomers may depress $v_f$ more than oligomers with higher $\overline{M}_n$. FROMP did not occur in resins including 0.5 and 1.0 kDA oligomers at loadings larger than 20 weight % and 30 weight %, respectively. By contrast, resins including 1.8 and 2.7 kDA oligomers demonstrated nearly similar $v_f$ values at loadings up to 40 weight %. The correlation between resin viscosity and $v_f$ is illustrated in FIG. 27.

Without being bound by theory, the oligomeric chain ends (specifically $=CH_2$) may engage in cross-metathesis reactions, representing a competitive pathway that may depress the local catalyst concentration by redirecting active catalyst species away from exothermic ring-opening metathesis reactions to net thermoneutral cross-metathesis processes. Further, shorter oligomers may contain a higher chain-end density, which may magnify the effect of competitive cross-metathesis reactions.

Figure 28:
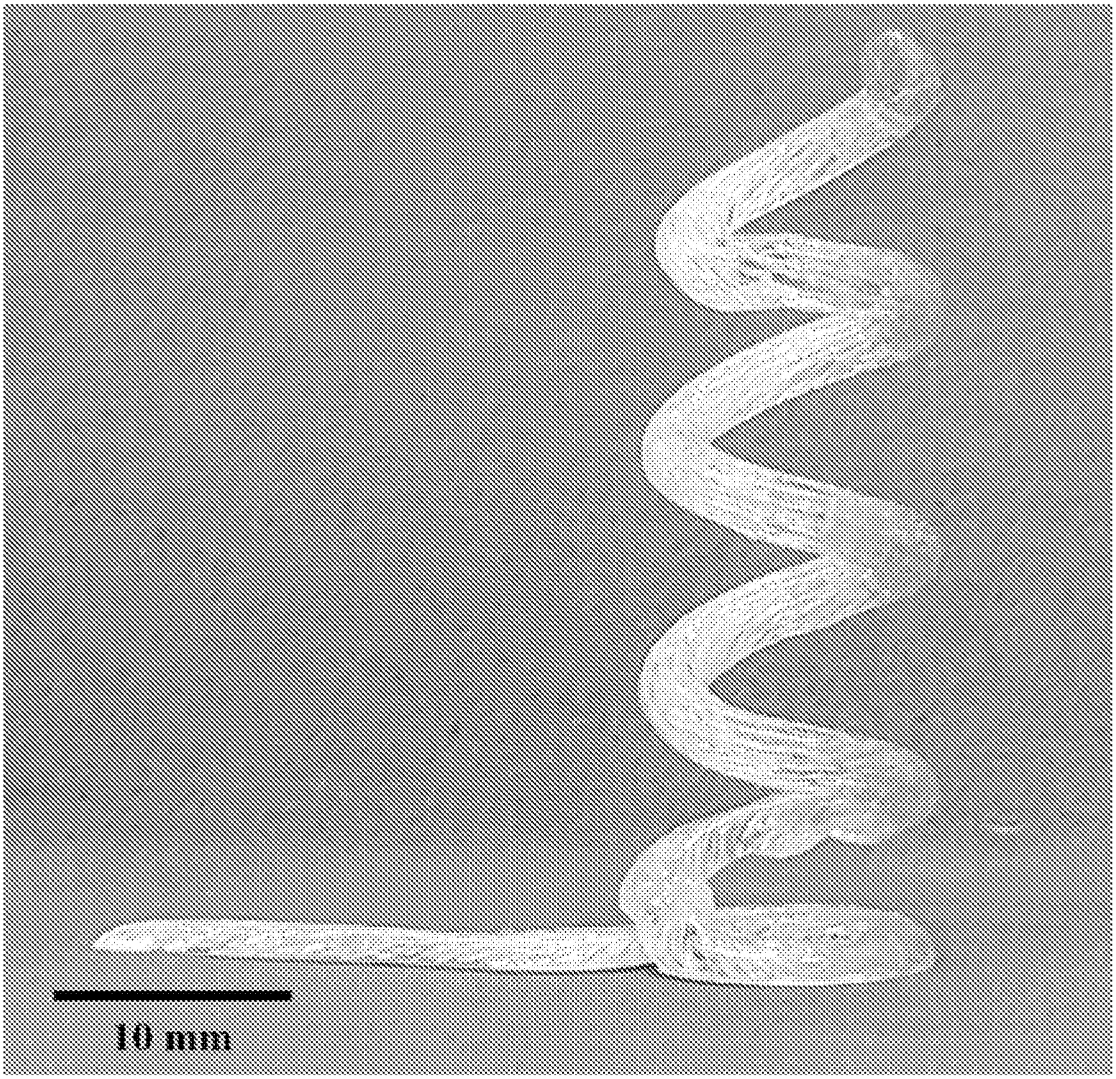
FIG. 28 illustrates an object prepared from rheologically modified FROMP resin with o(DCPD) ($\overline{M}_n$=2.7 kDa, 40 weight %), G2 (2.0 mM), DCPD, and ENB.
Figure 29A:
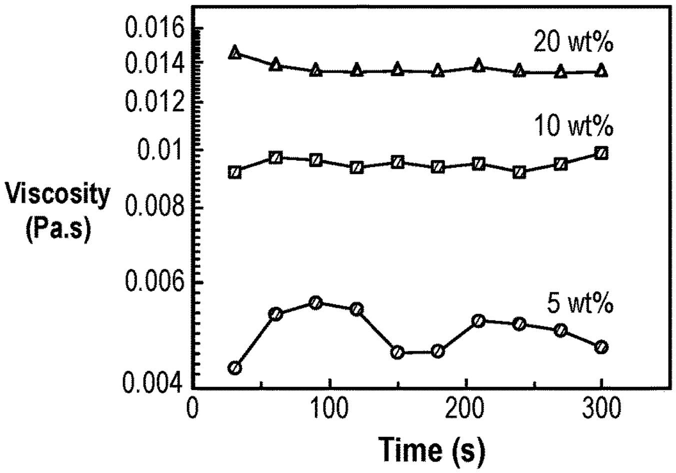
FIG. 29A illustrates a rheological profile for resins 15-17 including DCPD with 528 Da o(DCPD) fillers.
Figure 29B:
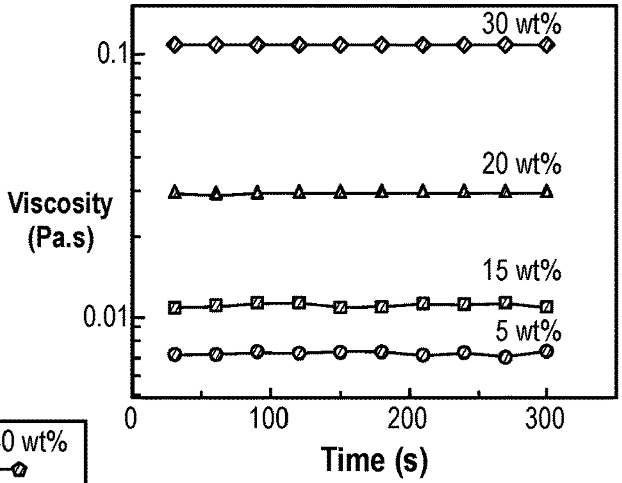
FIG. 29B illustrates a rheological profile for resins 18-21 including DCPD with 987 Da o(DCPD) fillers.
Figure 29C:
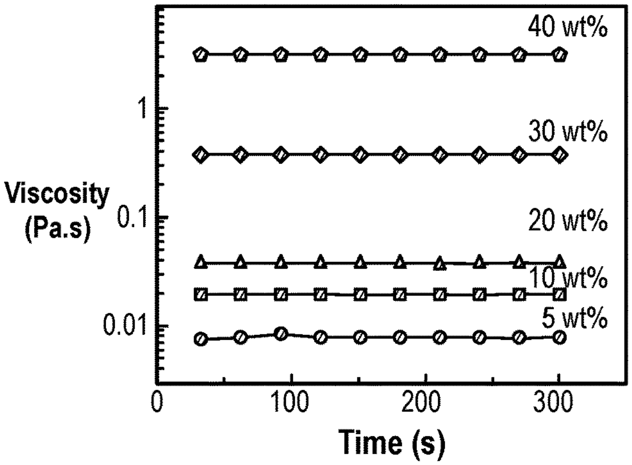
FIG. 29C illustrates a rheological profile for resins 22-26 including DCPD with 1820 Da o(DCPD) fillers.
Figure 29D:
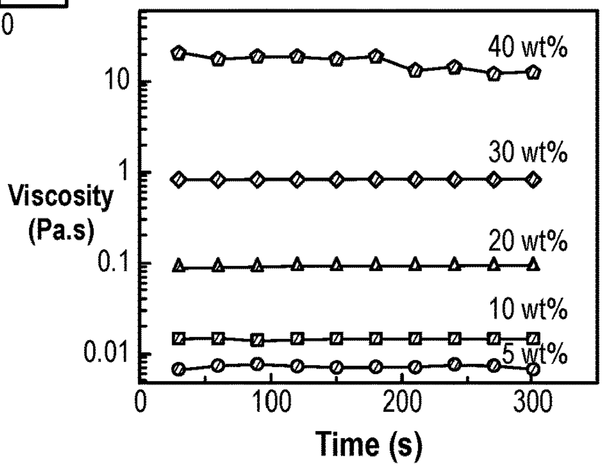
FIG. 29D illustrates a rheological profile for resins 27-31 including DCPD with 2674 Da o(DCPD) fillers.

One method to circumvent the observed depression in $v_f$ at higher oligomer loadings involves modulating the catalyst composition. Thickened resin of 10 Pa·s viscosities were prepared from the addition of 2.7 kDa oligomers (40 weight %). High catalyst loadings of G2 (2.0 mM) in the absence of $P(O^nBu)_3$ improved the observed catalytic rate, thereby increasing the heat-generation rate during FROMP reactions. Under the modified conditions, fronts traversed at a boosted $v_f$ of 0.5 mm·s$^{-1}$. The viscosity and $v_f$ of the boosted formulation were compatible with 3D-printing from an Aerotech 3D printer (14 Gauge Nozzle, 8.2 kPa working pressure). In the experimental setup, pre-chilled resin (2° C.) was extruded with a steady-state print head speed of 0.44 mm·s$^{-1}$ onto a heated surface (100° C.) to initiate FROMP. Subsequent propagation and curing occurred in a frontal fashion from the heat generated by polymerization. On-the-fly extrusion rate adjustments matched fluctuations in $v_f$ to enable high structural fidelity during printing. FIG. 28 illustrates an object prepared from rheologically modified FROMP resins with o(DCPD) ($\overline{M}_n$=2.7 kDa, 40 weight %), G2 (2.0 mM), and DCPD/ENB.

1. FROMP Reaction

Resins with different viscosities were prepared according to the following general procedure, which uses formulation 16 from Table 6 below as an example. Dicyclopentadiene (DCPD, 95.0 g, 720 mmol) and 5-ethylidene-2-norbornene (ENB, 5 g, 42 m) were mixed to produce a liquid resin ("DCPD:ENB"). Oligo-DCPD (1.0 g, $\overline{M}_n$=528) was added to 19.0 g of the DCPD:ENB resin in a vial, and the mixture was stirred until full dissolution of o(DCPD). In a second vial, G2 (4 mg, 6 μmol, 0.6 mM) and $P(O^nBu)_3$ (1.3 μL, 5 μmol, 0.5 mM) were dissolved in 200 μL of phenylcyclohexane, sonicated for 10 seconds, added to 10 mL of the DCPD:ENB:o(DCPD) resin, and vortexed for 30 seconds. The resin was added to a glass test tube, and FROMP was initiated with a hot soldering iron at the liquid-to-air interface using the FROMP initiation procedure.

TABLE 6

Composition of resin solutions at various DCPD:ENB to o(DCPD) mass ratios at fixed amounts of G2 (13 mg, 15 μmol) and $P(O^nBu)_3$ (4.2 μL, 16 μmol); o(DCPD) formulations from Table 1

| FROMP Formulation | o(DCPD) Formulation | o(DCPD) (g) | DCPD:ENB (g) | o(DCPD) (weight %) |
|---|---|---|---|---|
| 15 | 1 | 0.5 | 9.5 | 5 |
| 16 | 1 | 1.0 | 9.0 | 10 |
| 17 | 1 | 2.0 | 9.5 | 17 |
| 18 | 2 | 0.5 | 9.5 | 5 |
| 19 | 2 | 1.0 | 9.0 | 10 |
| 20 | 2 | 2.0 | 8.1 | 20 |
| 21 | 2 | 3.0 | 7.1 | 30 |
| 22 | 3 | 0.5 | 9.5 | 5 |
| 23 | 3 | 1.0 | 9.0 | 10 |
| 24 | 3 | 2.0 | 8.0 | 20 |
| 25 | 3 | 3.0 | 7.0 | 30 |
| 26 | 3 | 4.0 | 6.0 | 40 |
| 27 | 4 | 0.5 | 9.5 | 5 |
| 28 | 4 | 1.0 | 9.0 | 10 |
| 29 | 4 | 2.0 | 8.0 | 20 |
| 30 | 4 | 3.0 | 7.0 | 30 |
| 31 | 4 | 4.0 | 6.0 | 40 |

2. Resin Viscosity Determination

Isothermal viscosity measurements were performed on a TA Instruments Discovery HR-3 rheometer equipped with a 60-mm diameter aluminum parallel plate upper geometry and a 60-mm diameter temperature-controlled Peltier lower geometry. For each test, ≈1 mL of resin (Formulations 15-31) was loaded between the two plates (1200 μm loading gap; 1000 μm experimental gap). Time sweep measurements were performed at 20° C. for resin formulations 15-31. Each experiment was performed at 1.0% strain rate with a frequency of 10 rad·s$^{-1}$. Viscosity values are provided below in Table 7. Representative rheological curves are illustrated in FIGS. 29A-29D.

3. FROMP Initiation: Front Velocity and Temperature Profile Measurements

The resin formulations (15-31) described in Table 6 were transferred to 13×100 mm glass test tubes (total resin volume ≈3 mL). A K-type thermocouple (TMQSS, Omega) was inserted into the center of the test tube such that the tip was ≈1 cm below the surface of the resin. FROMP was initiated by direct contact of a hot 40 W soldering ion (Weller, WLC100) to the side of the glass test tube at a height corresponding to the surface of the resin solution. Front propagation was captured on a Samsung SM-G930V cellular phone equipped with a Dual Pixel 12.0 MP camera, which provided UHD 4K video footage (3840×2160 @ fps). The front velocities ($v_f$) were determined for each catalytic system from this recorded footage using the open-source physics (OSP) software package Tracker®. Temperature profiles (and maximum front temperatures, $T_{max}$) were recorded by the inserted thermocouple and monitored by a custom Labview program. The compiled $v_f$ and $T_{max}$ data for each catalyst system at all tested monomer compositions are illustrated in Table 7 below.

TABLE 7

Viscosities and frontal parameters ($T_{max}$ and $v_f$) associated with the modified DCPD:ENB resins

| FROMP Formulation | o(DCPD) Formulation | Vicosity · $10^{-3}$ (Pa · s) | $T_{max}$ (° C.) | $v_f$ (mm · s$^{-1}$) |
|---|---|---|---|---|
| 15 | 1 | 5.0 ± 0.4 | 163 ± 5 | 0.36 ± 0.02 |
| 16 | 1 | 9.4 ± 0.2 | 137 ± 15 | 0.09 ± 0.01 |
| 17 | 1 | 14 ± 0.3 | No FROMP | No FROMP |
| 18 | 2 | 7.2 ± 0.1 | 173 ± 3 | 0.69 ± 0.02 |
| 19 | 2 | 1.1 ± 0.2 | 150 ± 4 | 0.44 ± 0.06 |
| 20 | 2 | 29 ± 0.1 | 128 ± 16 | 0.18 ± 0.06 |
| 21 | 2 | 108 ± 0.2 | No FROMP | No FROMP |
| 22 | 3 | 7.9 ± 0.2 | 192 ± 19 | 1.03 ± 0.02 |
| 23 | 3 | 20 ± 0.4 | 162 ± 20 | 0.93 ± 0.05 |
| 24 | 3 | 37 ± 0.2 | 152 ± 10 | 0.69 ± 0.01 |
| 25 | 3 | 38 ± 1.2 | 132 ± 13 | 0.46 ± 0.07 |
| 26 | 3 | 320 ± 7.8 | 91 ± 1 | 0.07 ± 0.03 |
| 27 | 4 | 7.4 ± 0.2 | 178 ± 26 | 1.07 ± 0.08 |
| 28 | 4 | 14.3 ± 0.1 | 152 ± 7 | 0.72 ± 0.08 |
| 29 | 4 | 90 ± 1.0 | 128 ± 12 | 0.63 ± 0.06 |
| 30 | 4 | 840 ± 1.7 | 130 ± 10 | 0.29 ± 0.09 |
| 31 | 4 | 13000 ± 840 | 111 ± 7 | 0.24 ± 0.04 |

4. Three-Dimensional Printing

Resin for three-dimensional printing was prepared with the following example composition: (DCPD, 95 g, 720 mmol) and 5-ethylidene-2-norbornene (ENB, 5 g, 42 mmol) were mixed to produce a liquid resin (DCPD:ENB). Oligo-(DCPD) (o(DCPD), 10.1 g, $\overline{M}_n$ 2784) was added to 15.2 g of DCPD:ENB resin, and the mixture was mixed overnight using a tube revolver rotator. Then G2 (22 mg, 26 μmol, 1.0 mM) was added to the resin and then mixed until complete dissolution occurred. The resin was then transferred to a 10-mL syringe barrel (Norson-EFD) fitted with a 14-gauge nozzle (1.54 mm internal diameter). The resin was extruded with a pneumatic piston pump (HP10cc, Nordson-EFD).

The working pressure was set to 8.2 kPa and controlled by a pneumatic pressure dispensing unit (Ultimus V, Nordson-eFD). Free-standing structures were produced on a custom platform that controls motion, pneumatic pressure dispensing, and temperature. A motion controller (A3200, Aerotech Inc.) controlled the gantry (AGS1500-500-500, AeroTech Inc.) along 3 axes. A custom refrigeration system kept the printer head temperature fixed at 2° C. to prevent background polymerization (in other words, extends the working time) and slightly increases viscosity. The refrigeration system was cooled with an external refrigeration circulator (AP15R-40-A11B 15, Polyscience) and controlled by CN4216-R1-R2 from Omega Engineering Inc. FROMP was initiated on a heated bed (300×300 mm, 1.1 kW from E3D) set to 100° C. The steady-state print head velocity ($v_p$) was set to 0.44 mm·s$^{-1}$ to match the front velocity. For reliable steady-state behavior (in other words, $v_p$=$v_f$), the initial print head speed was 140% larger than at steady-state as the heat provided by the print bed accelerated the front velocity near the nozzle tip in the initial stages of printing.

In another example, a mixture of solid DCPD (10 g, 76 mmol, 4 equiv.) and solid oDCPD (2.5 g, 20 weight %) were heated to a melt with a heat gun. The resultant melt was cooled to ambient temperature and remained in a liquid state without crystallization or solidification. The viscosity of the melt at ambient temperature may be less than about 3 Pa·s, though viscosities up to 13 Pa·s may be observed for loadings of oDCPD at about 40 weight %. To the mixture, G2 (4.3 mg, 0.5 mM, 5 μmol) and P(O$^n$Bu)$_3$ (1.4 μL, 0.5 mm, 5 μmol) were added, and 6 mL of the FROMP resin was added to a 13×100 mm glass test tube. Thermal frontal polymerization was initiated with a hot soldering iron. After initiation, the exothermicity of FROMP provided a well-defined monomer-to-polymer reaction interface, which fully cured the resin within 1 minute ($v_f$≈0.4 to 0.8 mm·s$^{-1}$). The final polymer was translucent, which indicates that large-scale phase separation does not occur. The glass transition temperature of the polymer was determined to be $T_g$=140° C. by DSC with the following ramp rate: −50 to 225° C. (15° C.·min$^{-1}$), then 225 to −50° C. (15° C.·min$^{1}$), then −50 to 225° C.·min$^{-1}$ (5° C.·min$^{-1}$). $T_g$ is calculated as the midpoint of the thermal transition observed in the second heating cycle.

IV. Experimental Data

Table 8 provides a summary of characterization results of oligomers derived from Formulations 1-14 in Tables 1-4 above.

TABLE 8

| | Analytical Technique | $^{1}$H-NMR (End Group) | MALDI-TOF | | SEC (PS calibration) | | DSC |
|---|---|---|---|---|---|---|---|
| Monomer | Formulation | $\overline{M}_n$ (Da) | $\overline{M}_n$ (Da) | Đ | $\overline{M}_n$ (Da) | Đ | $T_g$ (° C.) |
| DCPD | 1 | 528 | 1819 | 1.16 | 900 ± 10.7% | 2.68 | 30 ± 7 |
| | 2 | 987 | 1865 | 1.31 | 1600 ± 10.7% | 3.14 | 55 ± 12 |
| | 3 | 1820 | 1974 | 1.21 | 3100 ± 10.7% | 3.78 | 75 ± 10 |
| | 4 | 2674 | 2299 | 1.18 | 7700 ± 10.7% | 4.17 | 103 ± 6 |
| ENB | 7 | 1544 | 2471 | 1.29 | 1900 ± 10.7% | 2.84 | — |
| | 8 | 2942 | 2661 | 1.31 | 4300 ± 10.7% | 3.06 | — |
| | 9 | 2264 | 2636 | 1.24 | 3000 ± 10.7% | 5.35 | — |
| | 10 | 6861 | 2654 | 1.40 | 10100 ± 10.7% | 4.26 | — |
| NBE | 11 | 717 | 1702 | 1.40 | 800 ± 10.7% | 3.25 | — |
| | 12 | 1172 | 1871 | 1.27 | 1500 ± 10.7% | 3.36 | — |
| DCPD[a] | 13 | 2525 | 2198 | 1.21 | 4700 ± 10.7% | 3.56 | — |
| DCPD[b] | 14 | 3448 | 2414 | 1.21 | 9400 ± 10.7% | 4.26 | — |

[a]3-Bromostyrene used as the CTA instead of styrene.
[b]EVE used as the CTA instead of styrene.

V. Oxidative Stability

Figure 30:
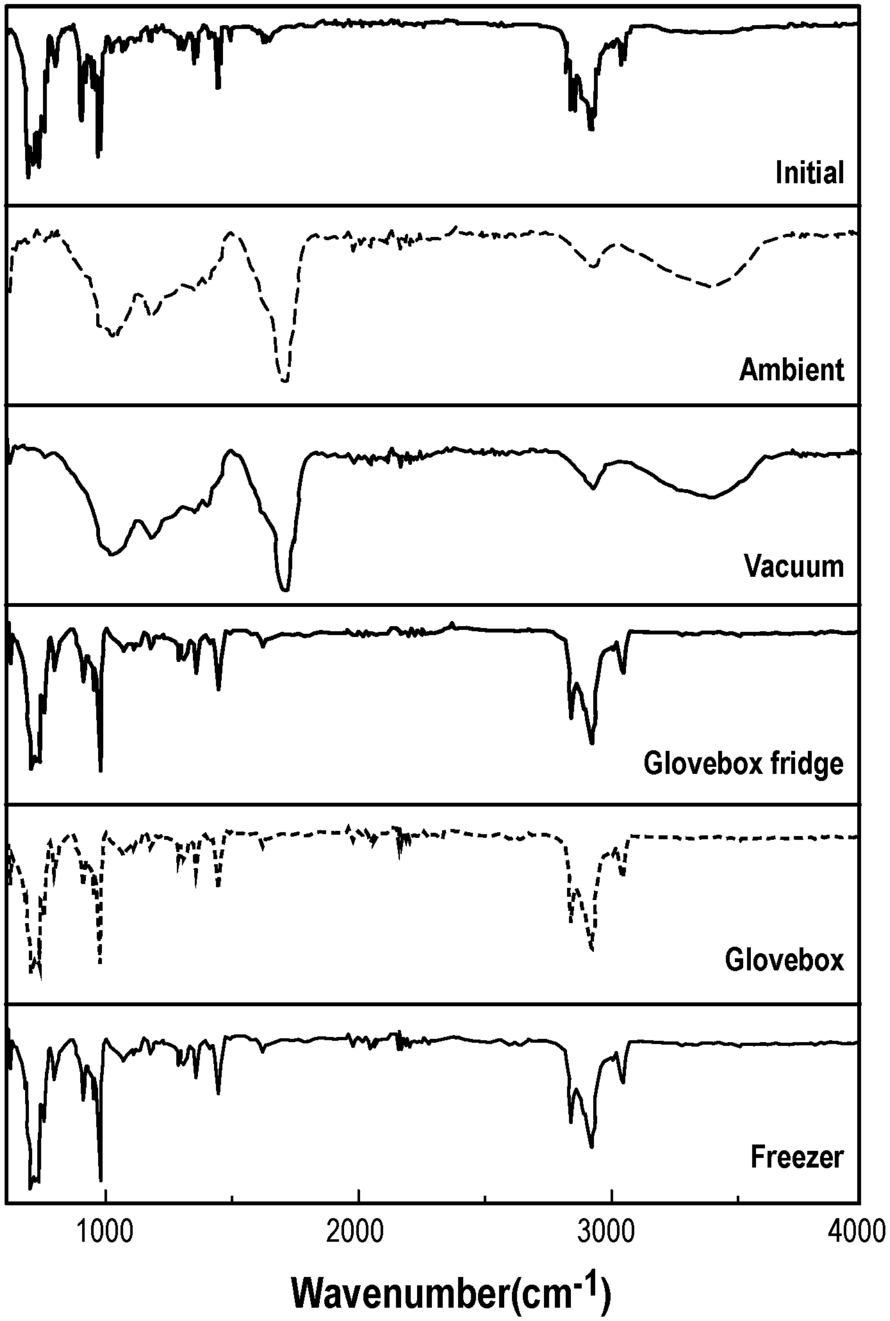
FIG. 30 illustrates FT-IR spectra of oxidation products of o(DCPD) derived from Formulation 2 after 7 days under various storage conditions.

The oligomers exhibited surprising sensitivity to background oxidation in the solid state under ambient conditions. By visual analysis, the initially white oligomers appeared to yellow over the span of a few days. The oxidized oligomers demonstrated significantly depressed solubilities, which suggests that oxidative cross-linking occurred. JR spectroscopy revealed the existence of oxygen incorporation, as illustrated in FIG. 30. New, broadened C═O (≈1700 cm$^{-1}$) and O—H (≈3300 cm$^{-1}$) stretching modes appeared after 7 days in air at ambient temperature. Proper storage conditions easily mitigated adventitious oxidation. The oligomers remained pristine for extended time spans at −30° C. in air, or at ambient temperatures under an inert atmosphere, as illustrated in FIG. 30.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the disclosure may also relate, among others, to the following aspects:

A first aspect relates to a method for preparing oligomers, comprising: adding an amount of a phosphite ester and an amount of a catalyst to an amount of a functionalized cycloalkene and an amount of a chain transfer agent to provide a mixture; and heating the mixture to produce the oligomers; wherein the chain transfer agent is a monosubstituted olefin; and wherein a degree of polymerization of the oligomers is controllable by a molar ration of the amount of the functionalized cycloalkene to the amount of the chain transfer agent.

A second aspect relates to the method of aspect 1, wherein the oligomers comprise an oligomer of formula (I):

(I)

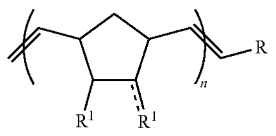

wherein R is a straight-chain, branched, or cyclic $(C_1-C_{20})$ alkyl group, or an aryl, heteroaryl, or heterocyclic group, optionally substituted with a boronate ester group, a hydroxy group, an epoxy group, an ester group, or an amide group; wherein each $R^1$ is independently hydrogen, a straight-chain, branched, or cyclic $(C_1-C_{20})$alkyl group or $(C_1-C_{20})$ alkenyl group; wherein ═══ represents an optional double bond, provided that when a double bond is present, the $R^1$ at one end of the double bond is not hydrogen; and wherein one or both $R^1$ groups of one monomer of the oligomer of formula (I) are the same or different than one or both $R^1$ groups of an adjacent monomer.

A third aspect relates to the method of aspect 1 or 2, wherein the oligomers are produced in a mass of at least about 1 gram.

A fourth aspect relates to the method of any one of aspects 1 to 3, wherein a second molar ratio of the amount of the catalyst to the amount of the functionalized cycloalkene is less than about 1:100.

A fifth aspect relates to the method of any one of aspects 1 to 4, wherein a second molar ratio of the amount of the catalyst to the amount of the functionalized cycloalkene is less than about 1:10000.

A sixth aspect relates to the method of any one of aspects 1 to 5, wherein the catalyst is a Grubbs catalyst.

A seventh aspect relates to the method of any one of aspects 1 to 6, wherein the catalyst is G2:

G2

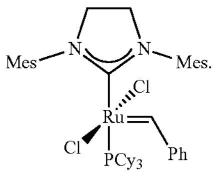

An eighth aspect relates to the method of any one of aspects 1 to 7, wherein the molar ratio is from about 1:1 to about 50:1.

A ninth aspect relates to the method of any one of aspects 1 to 8, wherein the amount of the functionalized cycloalkene is in a liquid phase.

A tenth aspect relates to the method of any one of aspects 1 to 9, wherein the heating the mixture comprises applying a heat source to the mixture at a temperature of from about 50 to about 500° C.

An eleventh aspect relates to the method of any one of aspects 1 to 10, wherein the degree of polymerization is a number-average degree of polymerization of from 3 to 30.

A twelfth aspect relates to the method of any one of aspects 1 to 11, wherein the method is free of solvent.

A thirteenth aspect relates to the method of any one of aspects 1 to 12, wherein when the molar ratio is about 5:1, an average degree of polymerization of the oligomers is 5.

A fourteenth aspect relates to the method of any one of aspects 1 to 12, wherein when the molar ratio is about 35:1, an average degree of polymerization of the oligomers is about 28.

A fifteenth aspect relates to the method of any one of aspects 1 to 14, wherein the functionalized cycloalkene is dicyclopentadiene, norbornene, 5-ethylidene-2-norbornene, or a combination thereof.

A sixteenth aspect relates to the method of any one of aspects 1 to 15, wherein the chain transfer agent is a monosubstituted olefin of formula (II):

(II)

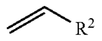

wherein $R^2$ is a straight-chain, branched, or cyclic $(C_1-C_{20})$ alkyl group or $(C_1-C_{20})$alkoxy group, or an aryl, heteroaryl, or heterocyclic group; and wherein the $(C_1-C_{20})$alkyl group, $(C_1-C_{20})$alkoxy group, aryl, heteroaryl, or heterocyclic group is optionally substituted with a halogen atom, a hydroxy group, a boronate ester group, an epoxy group, an ester group, or an amide group.

A seventeenth aspect relates to the method of any one of aspects 1 to 16, wherein the chain transfer agent is styrene, 3-bromostyrene, ethyl vinyl ether, or prop-2-en-1-ol.

An eighteenth aspect relates to a method of preparing a polymer from a second amount of the functionalized cycloalkene and the oligomers prepared by the method of any one of aspects 1 to 17, the method of preparing a polymer comprising: adding to the oligomers and the second amount of the functionalized cycloalkene a second amount of a phosphite ester and a second amount of the catalyst to provide a second mixture; and heating the second mixture to produce the polymer.

A nineteenth aspect relates to the method of preparing a polymer of aspect 18, wherein the second amount of the functionalized cycloalkene and the oligomers are a melt having a viscosity at ambient temperature of less than about 20 Pa·s.

A twentieth aspect relates to the method of preparing a polymer of aspect 18 or 19, wherein a third molar ratio of the second amount of the catalyst to the second amount of the functionalized cycloalkene is less than about 1:100.

A twenty-first aspect relates to the method of preparing a polymer of any one of aspects 18 to 20, wherein a third molar ratio of the second amount of the catalyst to the second amount of the functionalized cycloalkene is less than about 1:10000.

A twenty-second aspect relates to the method of preparing a polymer of any one of aspects 18 to 21, wherein the heating the second mixture comprises applying a heat source to the second mixture at a temperature of from about 50 to about 500° C.

A twenty-third aspect relates to the method of preparing a polymer of any one of aspects 18 to 22, wherein the method of preparing a polymer is free of solvent.

A twenty-fourth aspect relates to a method of preparing oligomers of formula (Ia), comprising:

(Ia)

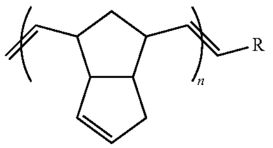

adding an amount of a phosphite ester of formula $P(OR^3)_3$ and an amount of a catalyst to an amount of dicyclopentadiene and an amount of a chain transfer agent to provide a mixture; and heating the mixture to produce the oligomers of formula (Ia); wherein R is a straight-chain, branched, or cyclic $(C_1\text{-}C_{20})$alkyl group, or an aryl, heteroaryl, or heterocyclic group, optionally substituted with a boronate ester group, a hydroxy group, an epoxy group, an ester group, or an amide group; wherein $R^3$ are all simultaneously or each independently methyl, ethyl, n-butyl, tert-butyl, or phenyl; wherein the chain transfer agent is a monosubstituted olefin of formula (II):

(II)

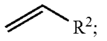

wherein $R^2$ is a straight-chain, branched, or cyclic $(C_1\text{-}C_{20})$ alkyl group or $(C_1\text{-}C_{20})$alkoxy group, or an aryl, heteroaryl, or heterocyclic group, the $(C_1\text{-}C_{20})$alkyl group, $(C_1\text{-}C_{20})$ alkoxy group, aryl, heteroaryl, or heterocyclic group optionally substituted with a halogen atom, a hydroxy group, a boronate ester group, an epoxy group, an ester group, or an amide group; and wherein a degree of polymerization of the oligomers of formula (Ia) is controllable by a molar ratio of the amount of dicyclopentadiene to the amount of the chain transfer agent.

A twenty-fifth aspect relates to the method of aspect 24, wherein the oligomers of formula (Ia) are produced in a mass of at least about 1 gram.

A twenty-sixth aspect relates to the method of aspect 24 or 25, wherein a second molar ratio of the amount of the catalyst to the amount of dicyclopentadiene is less than about 1:100.

A twenty-seventh aspect relates to the method of any one of aspects 24 to 26, wherein a second molar ratio of the amount of the catalyst to the amount of dicyclopentadiene is less than about 1:10000.

A twenty-eighth aspect relates to the method of any one of aspects 24 to 27, wherein the catalyst is a Grubbs catalyst.

A twenty-ninth aspect relates to the method of any one of aspects 24 to 28, wherein the catalyst is G2:

G2

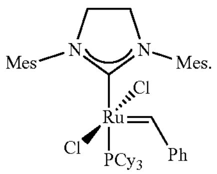

A thirtieth aspect relates to the method of any one of aspects 24 to 29, wherein the molar ratio is from about 1:1 to 50:1.

A thirty-first aspect relates to the method of any one of aspects 24 to 30, wherein the amount of dicyclopentadiene is in a liquid phase.

A thirty-second aspect relates to the method of any one of aspects 24 to 31, wherein the heating the mixture comprises applying a heat source to the mixture at a temperature of from about 50 to about 500° C.

A thirty-third aspect relates to the method of any one of aspects 24 to 32, wherein R is substituted with a boronate ester group, a hydroxy group, an alkoxy group, an epoxy group, an ester group, or an amide group.

A thirty-fourth aspect relates to the method of any one of aspects 24 to 33, wherein the degree of polymerization is a number-average degree of polymerization of from 3 to 30.

A thirty-fifth aspect relates to the method of any one of aspects 24 to 34, wherein the method is free of solvent.

A thirty-sixth aspect relates to the method of any one of aspects 24 to 35, wherein when the molar ratio is about 5:1, an average degree of polymerization of the oligomers of formula (Ia) is 5.

A thirty-seventh aspect relates to the method of any one of aspects 24 to 35, wherein when the molar ratio is about 35:1, an average degree of polymerization of the oligomers of formula (Ia) is 28.

A thirty-eighth aspect relates to a composition, comprising dicyclopentadiene and oligomers of formula (I):

(I)

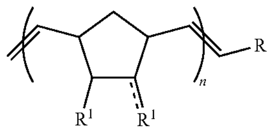

wherein the oligomers of formula (I) are in an amount of from about 20 weight % to about 80 weight % based on a combined 100 weight % of the oligomers of formula (I) and the dicyclopentadiene; wherein a number-average degree of polymerization of the oligomers of formula (I) is from 3 to 30; wherein R is a straight-chain, branched, or cyclic $(C_1\text{-}C_{20})$alkyl group, or an aryl, heteroaryl, or heterocyclic group, optionally substituted with a boronate ester group, a hydroxy group, an epoxy group, an ester group, or an amide group; wherein each $R^1$ may independently be hydrogen, a straight-chain, branched, or cyclic $(C_1\text{-}C_{20})$alkyl group or $(C_1\text{-}C_{20})$alkenyl group; wherein ═══ represents an optional double bond, provided that when a double bond is present, the $R^1$ at one end of the double bond is not hydrogen; and wherein one or both $R^1$ groups of one monomer of the oligomers of formula (I) are the same as, or different than, one or both $R^1$ groups of an adjacent monomer.

A thirty-ninth aspect relates to the composition of aspect 38, wherein R is a boronate ester group, a hydroxy group, an alkoxy group, an epoxy group, an ester group, or an amide group.

A fortieth aspect relates to the composition of aspect 38 or 39, wherein the composition is a melt having a viscosity at ambient temperature of less than about 20 Pa·s.

A forty-first aspect relates to a method of preparing a polymer from the composition of any one of aspects 38 to 40, comprising: adding to the composition an amount of a phosphite ester of formula $P(OR^3)_3$ and an amount of a catalyst to provide a mixture; and heating the mixture to produce the polymer; and wherein $R^3$ are all simultaneously or each independently methyl, ethyl, n-butyl, tert-butyl, or phenyl.

A forty-second aspect relates to the method of aspect 41, wherein a molar ratio of the amount of the catalyst to the amount of dicyclopentadiene is less than about 1:100.

A forty-third aspect relates to the method of aspect 41 or 42, wherein the catalyst is a Grubbs catalyst.

A forty-fourth aspect relates to the method of any one of aspects 41 to 43, wherein the catalyst is G2:

G2

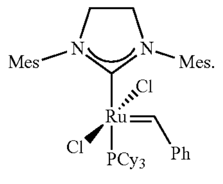

A forty-fifth aspect relates to the method of any one of aspects 41 to 44, wherein the heating the mixture comprises applying a heat source to the mixture at a temperature of from about 50 to about 500° C.

A forty-sixth aspect relates to the method of any one of aspects 41 to 45, wherein a glass transition temperature of the polymer is about 140° C. as measured by differential scanning calorimetry.

A forty-seventh aspect relates to the method of any one of aspects 41 to 46, wherein the method is free of solvents.

In addition to the features mentioned in each of the independent aspects enumerated above, some examples may show, alone or in combination, the optional features mentioned in the dependent aspects and/or as disclosed in the description above and shown in the figures.

What is claimed is:

1. A method for preparing oligomers, comprising:

adding an amount of a phosphite ester and an amount of a catalyst to an amount of a functionalized cycloalkene and an amount of a chain transfer agent to provide a mixture; and heating the mixture to produce the oligomers;

wherein the chain transfer agent is a monosubstituted olefin;

wherein a degree of polymerization of the oligomers is controlled by a molar ratio of the amount of the functionalized cycloalkene to the amount of the chain transfer agent, and wherein the degree of polymerization is a number-average degree of polymerization of from 3 to 30.

2. The method of claim 1, wherein the oligomers are produced in a mass of at least 1 gram.

3. The method of claim 1, wherein a molar ratio of the amount of the catalyst to the amount of the functionalized cycloalkene is less than 1:100.

4. The method of claim 1, wherein the functionalized cycloalkene is dicyclopentadiene, norbornene, 5-ethylidene-2-norbornene, or a combination thereof.

5. The method of claim 1, wherein the chain transfer agent is a monosubstituted olefin of formula (II):

(II)

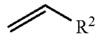

wherein $R^2$ is a straight-chain, branched, or cyclic $(C_1-C_{20})$alkyl group or $(C_1-C_{20})$alkoxy group, or an aryl, heteroaryl, or heterocyclic group;

wherein the $(C_1-C_{20})$alkyl group, $(C_1-C_{20})$alkoxy group, aryl, heteroaryl, or heterocyclic group is optionally substituted with a halogen atom, a hydroxy group, a boronate ester group, an epoxy group, an ester group, or an amide group.

6. The method of claim 1 wherein the chain transfer agent is styrene, 3-bromostyrene, ethyl vinyl ether, or prop-2-en-1-ol.

7. The method of claim 1, wherein the molar ratio is from about 1:1 to about 50:1.

8. The method of claim 1, wherein the heating the mixture comprises applying a heat source to the mixture at a temperature of from about 50 to about 500° C.

9. The method of claim 1, wherein the method is free of solvent.

10. The method of claim 1, wherein when the molar ratio is about 5:1, an average degree of polymerization of the oligomers is 5.

11. The method of claim 1, wherein when the molar ratio is about 35:1, an average degree of polymerization of the oligomers is about 28.

12. A method of preparing a polymer from a second amount of the functionalized cycloalkene and the oligomers prepared by the method of claim 1, the method of preparing a polymer comprising:

adding to the oligomers and the second amount of the functionalized cycloalkene a second amount of a phosphite ester and a second amount of the catalyst to provide a second mixture; and heating the second mixture to produce the polymer.

13. A method for preparing chain-terminated oligomers, comprising:

adding an amount of a phosphite ester and an amount of a catalyst to an amount of a functionalized cycloalkene and an amount of a chain transfer agent to provide a mixture; and heating the mixture to produce the chain-terminated oligomers as a majority product;

wherein the chain transfer agent is a monosubstituted olefin;

wherein a degree of polymerization of the oligomers is controlled by a molar ratio of the amount of the functionalized cycloalkene to the amount of the chain transfer agent, wherein the oligomers comprise an oligomer of formula (I):

(I)

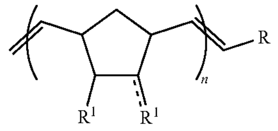

wherein R is a straight-chain, branched, or cyclic $(C_1-C_{20})$alkyl group, or an aryl, heteroaryl, or heterocyclic group, optionally substituted with a boronate ester group, a hydroxy group, an epoxy group, an ester group, or an amide group;

wherein each $R^1$ is independently hydrogen, a straight-chain, branched, or cyclic $(C_1-C_{20})$alkyl group or $(C_1-C_{20})$alkenyl group;

wherein ═══ represents an optional double bond, provided that when a double bond is present, the $R^1$ at one end of the double bond is not hydrogen; and wherein one or both $R^1$ groups of one monomer of the oligomer of formula (I) are the same or different than one or both $R^1$ groups of an adjacent monomer.

14. A method of preparing chain-terminated oligomers of formula (Ia), comprising:

(Ia)

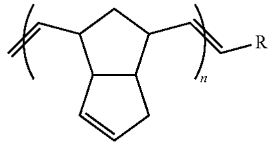

adding an amount of a phosphite ester of formula $P(OR^3)_3$ and an amount of a catalyst to an amount of dicyclopentadiene and an amount of a chain transfer agent to provide a mixture; and heating the mixture to produce the chain-terminated oligomers of formula (Ia) as a majority product;

wherein R is a straight-chain, branched, or cyclic ($C_1$-$C_{20}$)alkyl group, or an aryl, heteroaryl, or heterocyclic group, optionally substituted with a boronate ester group, a hydroxy group, an epoxy group, an ester group, or an amide group;

wherein $R^3$ are all simultaneously or each independently methyl, ethyl, n-butyl, tert-butyl, or phenyl;

wherein the chain transfer agent is a monosubstituted olefin of formula (II):

(II)

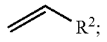

wherein $R^2$ is a straight-chain, branched, or cyclic ($C_1$-$C_{20}$)alkyl group or ($C_1$-$C_{20}$)alkoxy group, or an aryl, heteroaryl, or heterocyclic group, the ($C_1$-$C_{20}$)alkyl group, ($C_1$-$C_{20}$)alkoxy group, aryl, heteroaryl, or heterocyclic group optionally substituted with a halogen atom, a hydroxy group, a boronate ester group, an epoxy group, an ester group, or an amide group; and wherein a degree of polymerization of the chain-terminated oligomers of formula (Ia) is controlled by a molar ratio of the amount of dicyclopentadiene to the amount of the chain transfer agent.

15. The method of claim 14, wherein the method is free of solvents.

16. The method of claim 14, wherein when the molar ratio is about 5:1, an average degree of polymerization of the oligomers of formula (Ia) (I) is 5.

17. The method of claim 14, wherein when the molar ratio is about 35:1, an average degree of polymerization of the oligomers is 28.

18. The method of claim 14, wherein the yield for the chain-terminated oligomers of formula (Ia) is at least 42%.

19. The method of claim 14, wherein the yield for the chain-terminated oligomers of formula (Ia) is at least 62%.

20. The method of claim 14, wherein the yield for the chain-terminated oligomers of formula (Ia) is at least 80%.

21. The method of claim 14, wherein the yield for the chain-terminated oligomers of formula (Ia) is at least 95%.

22. A composition, comprising dicyclopentadiene and oligomers of formula (I):

(I)

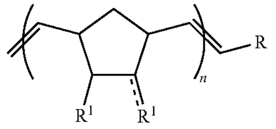

wherein the oligomers of formula (I) are in an amount of from about 20 weight % to about 80 weight % based on a combined 100 weight % of the oligomers of formula (I) and the dicyclopentadiene;

wherein a number-average degree of polymerization of the oligomers of formula (I) is from 3 to 30;

wherein R is a straight-chain, branched, or cyclic ($C_1$-$C_{20}$)alkyl group, or an aryl, heteroaryl, or heterocyclic group, optionally substituted with a boronate ester group, a hydroxy group, an epoxy group, an ester group, or an amide group;

wherein each $R^1$ may independently be hydrogen, a straight-chain, branched, or cyclic ($C_1$-$C_{20}$)alkyl group or ($C_1$-$C_{20}$)alkenyl group;

wherein ═══ represents an optional double bond, provided that when a double bond is present, the $R^1$ at one end of the double bond is not hydrogen; and wherein one or both $R^1$ groups of one monomer of the oligomers of formula (I) are the same as, or different than, one or both $R^1$ groups of an adjacent monomer.

23. A method of preparing a polymer from the composition of claim 22, comprising:

adding to the composition an amount of a phosphite ester of formula $P(OR^3)_3$ and an amount of a catalyst to provide a mixture; and heating the mixture to produce the polymer; and wherein $R^1$ are all simultaneously or each independently methyl, ethyl, n-butyl, tert-butyl, or phenyl.

* * * * *